(12) United States Patent
Ametamey et al.

(10) Patent No.: US 9,771,368 B2
(45) Date of Patent: Sep. 26, 2017

(54) $^{18}$F-LABELLED FOLATES

(71) Applicant: MERCK & CIE, Schaffhausen (CH)

(72) Inventors: Simon Mensah Ametamey, Zurich (CH); Rudolf Moser, Schaffhausen (CH); Tobias Ludwig Ross, Zurich (CH); Viola Groehn, Dachsen (CH)

(73) Assignee: MERCK & CIE, Schaffhausen (CH)

( * ) Notice: Subject to any disclaimer, the term of this patent is extended or adjusted under 35 U.S.C. 154(b) by 0 days.

(21) Appl. No.: 15/042,657

(22) Filed: Feb. 12, 2016

(65) Prior Publication Data

US 2016/0159802 A1    Jun. 9, 2016

Related U.S. Application Data

(62) Division of application No. 12/595,301, filed as application No. PCT/EP2008/054408 on Apr. 11, 2008, now Pat. No. 9,315,506.

(30) Foreign Application Priority Data

Apr. 11, 2007 (EP) .................................. 07105987

(51) Int. Cl.
  *G01N 33/62* (2006.01)
  *C07D 475/08* (2006.01)
  (Continued)

(52) U.S. Cl.
  CPC ........ *C07D 475/08* (2013.01); *A61K 51/0459* (2013.01); *A61K 51/0497* (2013.01);
  (Continued)

(58) Field of Classification Search
  None
  See application file for complete search history.

(56) References Cited

U.S. PATENT DOCUMENTS

5,698,556 A    12/1997  Chan
6,894,161 B2    5/2005  Desjardins et al.
(Continued)

FOREIGN PATENT DOCUMENTS

CN    1962658 A    5/2007
EP    0031237 A1    7/1981
(Continued)

OTHER PUBLICATIONS

Tewson, Timothy J., et al., "Preparation of Fluorine-18 Aryl Fluorides: Piperidyl Triazenes as a Source of Diazonium Salts", J. Chem. Soc., Chem. Commun. 1979, 1149-1150.
(Continued)

*Primary Examiner* — Anna Pagonakis
(74) *Attorney, Agent, or Firm* — Millen White Zelano and Branigan, PC; Csaba Henter; Anthony Zelano

(57) ABSTRACT

The present invention is directed towards new $^{18}$F-folate radiopharmaceuticals, wherein the fluorine-18 is covalently linked to the aminobenzoyl moiety, which connects the condensed pyrimidine heterocycle to the amino acid portion within folate structures, as well as their precursors and their non-radioactive references, a method of their preparation, as well as their use in diagnosis of a cell or population of cells expressing a folate-receptor and monitoring of cancer and inflammatory and autoimmune diseases and therapy thereof.

21 Claims, 4 Drawing Sheets

(51) Int. Cl.
*A61K 51/04* (2006.01)
*C07D 475/04* (2006.01)
*G01N 33/574* (2006.01)
*G01N 33/60* (2006.01)
*G01N 33/82* (2006.01)

(52) U.S. Cl.
CPC ..... *C07D 475/04* (2013.01); *G01N 33/57492* (2013.01); *G01N 33/60* (2013.01); *G01N 33/82* (2013.01); *C07B 2200/05* (2013.01); *G01N 2333/705* (2013.01)

(56) References Cited

U.S. PATENT DOCUMENTS

| 8,344,140 B2 | 1/2013 | Ametamey et al. |
| 2007/0276231 A1 | 11/2007 | Low et al. |

FOREIGN PATENT DOCUMENTS

| EP | 0344922 | A2 | 12/1989 |
| WO | 8904307 | A1 | 5/1989 |
| WO | 9216512 | A1 | 10/1992 |
| WO | 9315077 | A1 | 8/1993 |
| WO | 9319051 | A1 | 9/1993 |
| WO | 9920626 | A1 | 4/1999 |
| WO | 02085908 | A1 | 10/2002 |
| WO | 2004069159 | A2 | 8/2004 |
| WO | 2004071463 | A2 | 8/2004 |
| WO | 2006014706 | A2 | 2/2006 |
| WO | 20060171754 | A | 7/2006 |
| WO | 2007098089 | A2 | 8/2007 |
| WO | 2007139815 | A2 | 12/2007 |

OTHER PUBLICATIONS

Kilbourn, Michael R., et. al., "Carrier-Added and No-Carrier-Added Synthesis of [18F]Spiroperidol and [18F] Haloperidol", Int. J. Appl. Radial Isot. vol. 35(7), 591-598, 1984.
Holmes et al., "Synthesis and Characterization of 2'-Azidoaminopterin as a Potential Photoaffinity Label for Folate-Utilizing Enzymes" Biorganic Chemistry 11, 281-299 (1982).
Isotopes of Fluorine from Wikipedia printed Sep. 29, 2015, pp. 1-3.
Nakamura et al., "Nitration and chlorination of folic acid by peroxynitrite and hypochlorous acid, and the selective binding of 10-nitro-folate to folate receptor beta". Biochemical and Biophysical Research Communications, 297, 1238-1244, 2002.
Bartlett et al., "Evaluation of potent inhibitors of dihydrofolate reductase in a culture model for growth of pneumocystis carinii". Antimicrobial agents and chemotherapy, Nov. 1995, p. 2436-2441.
Henkin et al., "Novel fluorinated antifolates. Enzyme inhibition and cytocoxicity studies on 2' and 3'fluoroaminopterin". J. Med. Chem. 1983, 26, 1193-1196.
Marik et al., Click for PET: "rapid preparation of [18]fluoropeptides using CuI catalyzed 1,3-dipolar cycloaddition". Tet. Letter, vol. 47 (No. 37), 2006, pp. 6681-6684.
International Search Report of PCT/EP2008/054408 (May 5, 2009).
J.A. Montgomery et al., "3'-Fluorofolic Acid", Journal of Medicinal Chemistry, vol. 8, No. 5 (Sep. 1965) pp. 727-728.
Bettio et al., "Synthesis and preclinical evaluation of a folic acid derivative labeled with 18F for PET Imaging of folate receptor-positive tumors". J. Nuclear Medicine, vol. 47, 2005, pp. 1153-1160, especially p. 1156.

18F-LABELLED FOLATES

FIELD OF INVENTION

The present invention is directed towards new $^{18}$F-folate radiopharmaceuticals, wherein fluorine-18 is covalently linked to the aminobenzoyl moiety, which connects the condensed pyrimidine heterocycle to the amino acid portion within folate structures, as well as their precursors, a method of their preparation, as well as their use in diagnosis of a cell or population of cells expressing a folate-receptor and monitoring of cancer and inflammatory and autoimmune diseases and therapy thereof.

BACKGROUND

Cell-specific targeting for delivery of effector moieties such as diagnostic or therapeutic agents is a widely researched field and has led to the development of non-invasive diagnostic and/or therapeutic medical applications. In particular in the field of nuclear medicine procedures and treatments, which employ radioactive materials emitting electromagnetic radiations as γ-rays or particle emitting radiation, selective localization of these radioactive materials in targeted cells or tissues is required to achieve either high signal intensity for visualization of specific tissues, assessing a disease and/or monitoring effects of therapeutic treatments, or high radiation dose, for delivering adequate doses of ionizing radiation to a specified diseased site, without the risk of radiation injury in other e.g. healthy tissues. It is thus of crucial interest to determine and assess cell-specific structures and in particular structures that are present in case of cancer (i.e. tumors) or inflammatory and autoimmune diseases, such as receptors, antigens, haptens and the like which can be specifically targeted by the respective biological vehicles.

The folate receptor (FR) has been identified as one of these structures. The FR is a high-affinity ($K_D < 10^{-9}$ M) membrane-associated protein. In normal tissues and organs FR-expression is highly restricted to only a few organs (e.g. kidney, lungs, choroids plexus, and placenta), where it largely occurs at the luminal surface of epithelial cells and is therefore not supplied with folate in the circulation. The FR-alpha is frequently overexpressed on a wide variety of specific cell types, such as epithelial tumours (e.g. ovarian, cervical, endometrial, breast, colorectal, kidney, lung, nasopharyngeal), whereas the FR-beta is frequently overexpressed in leukaemia cells (approx. 70% of acute myelogenous leukaemia (AML) are FR-beta positive). Both may therefore be used as a valuable tumour marker for selective tumour-targeting (Elnakat and Ratnam, Adv. Drug Deliv. Rev. 2004; 56:1067-84). In addition it has recently been discovered that activated (but not resting) synovial macrophages in patients diagnosed with rheumatoid arthritis possess a functionally active FR-beta (Nakashima-Matsushita et al, Arthritis & Rheumatism, 1999, 42(8): 1609-16). Therefore activated macrophages can be selectively targeted with folate conjugates in arthritic joints, a capability that opens possibilities for the diagnosis and treatment of rheumatoid arthritis (Paulos et al, Adv. Drug Deliv. Rev. 2004; 56:1205-17).

Folates is used herein as a generic term for a family of chemically-similar compounds involved in a range of biosynthetic pathways. Folates consist of three units, which include (i) a condensed pyrimidine heterocycle unit, which is linked via a methylene group at the C-6 position to (ii) a p-aminobenzoic acid unit, which is linked to (iii) one or more amino acid units. For example, in the case of folic acid derivatives, a pteridine heterocycle unit is linked via a methylene group at the C-6 position to a p-aminobenzoic acid unit, which is linked to a variable number of glutamic acid units. Each of those three units may be subjected to variation to create a library of various folate structures. Such variations may include folates, that differ in the oxidation state of the pteridine ring, the type of the one carbon substituent at N5 and/or N10 positions, the type and number of conjugated amino acid residues, and the substitution pattern of the various units. Folic acid itself as a synthetic analogue and member of the group of folates is the most oxidized form, whereas dihydrofolate and tetrahydrofolate are progressively more reduced forms of folates (as their name indicates).

Folates are involved in the transfer of 1-C units in key synthetic pathways of bio-molecules such as methionine, purine, and pyrimidine biosynthesis. Additionally, they play an important role in the interconversion of serine and glycine, and in histidine catabolism. Folates and its derivatives have thus been intensively studied over the past 15 years as targeting agents for the delivery of therapeutic and/or diagnostic agents to cell populations bearing folate receptors in order to achieve a selective concentration of therapeutic and/or diagnostic agents in such cells relative to normal cells.

Various probes have been conjugated to folic acid and (pre)clinically evaluated, including folate radiopharmaceuticals (Leamon and Low, Drug Discov. Today 2001; 6:44-51 and Jammaz et al, J. Label Compd Radiopharm 2006; 49:125-137), folate-conjugates of chemotherapeutic agents (Leamon and Reddy, Adv. Drug Deliv. Rev. 2004; 56:1127-41; Leamon et al, Bioconjugate Chem. 2005; 16:803-11), proteins and protein toxins (Ward et al, J. Drug Target. 2000; 8:119-23; Leamon et al, J. Biol. Chem. 1993; 268:24847-54; Leamon and Low, J. Drug Target. 1994; 2:101-12), antisense oligonucleotides (Li et al, Pharm. Res. 1998; 15:1540-45; Zhao and Lee, Adv. Drug Deliv. Rev. 2004; 56:1193-204), liposomes (Lee and Low, Biochim. Biophys. Acta-Biomembr. 1995; 1233:134-44; Gabizon et al, Adv. Drug Deliv. Rev. 2004; 56:1177-92), hapten molecules (Paulos et al, Adv. Drug Deliv. Rev. 2004; 56:1205-17), MRI contrast agents (Konda et al, Magn. Reson. Mat. Phys. Biol. Med. 2001; 12:104-13) etc. Typically all of these probes are conjugated to folic acid through its glutamate portion which lends itself to known carboxylic acid coupling methodology.

Folate radiopharmaceuticals can be in particular very useful for an improved diagnosis and evaluation of the effectiveness of cancer therapy. This may include assessment and/or prediction of a treatment response and consequently improvement of radiation dosimetry. Typical visualization techniques suitable for radioimaging are known in the art and include positron emission tomography (PET), planar or single photon emission computerized tomography (SPECT) imaging, gamma cameras, scintillation, and the like.

Both PET and SPECT use radiotracers to image, map and measure activities of target sites of choice. Yet, while PET uses positron emitting nuclides which require a nearby cyclotron due to the short half-lives of the positron emitters, SPECT uses single photon emitting nuclides which are available by generator systems, which may make its use independent of nearby facilities such as cyclotrons or reactors and thus more convenient. However SPECT provides less sensitivity than PET and besides a few approaches quantification methods are lacking. In contrast, PET PET shows a higher sensitivity (more than 100-fold of SPECT)

and provides well-elaborated quantification methods. Moreover, PET is one of the most sophisticated functional imaging technologies to assess regional uptake and affinity of ligands or metabolic substrates in brain and other organs and thus provides measures of imaging based on metabolic activity. This is for example achieved by administering a positron emitting nuclide to a subject, and as it undergoes radioactive decay the gamma rays resulting from the positron annihilation are detected in the PET scanner by a ring of detectors which are coincidentally connected in pairs.

Factors that need to be considered in the selection of a suitable isotope useful for PET include sufficient half-life of the positron-emitting isotope to permit preparation of a diagnostic composition optionally in a pharmaceutically acceptable carrier prior to administration to the patient, and sufficient remaining half-life to yield sufficient activity to permit extra-corporeal measurement by a PET scan. Furthermore, a suitable isotope should have a sufficiently short half-life to limit patient exposure to unnecessary radiation. Typically, a suitable radiopharmaceutical for PET may be based on a metal isotope, such as gallium or copper. These two require however a chelator for entrapment of the metal, which may have an effect on steric and chemical properties. Alternatively a radiopharmaceutical may be based on a covalently linked isotope which provides minimal structural alteration. Radionuclides used for covalent attachment and suitable for PET scanning are typically positron emitting isotopes with short half lives such as $^{11}C$ (ca. 20 min), $^{13}N$ (ca. 10 min), $^{15}O$ (ca. 2 min) and $^{18}F$ (ca. 110 min).

To date, a number of chelate-based folate radiopharmaceuticals have been synthesized and successfully evaluated as diagnostic agents for imaging folate receptor-positive tumors. The most widely studied derivatives were labeled either with $^{111}$In and $^{99m}$Tc (Siegel et al., J. Nucl. Med. 2003, 44:700; Müller et al., J. Organomet. Chem. 2004, 689:4712) or with $^{68}$Ga (Mathias et al., Nucl. Med. Biol. 2003, 30(7): 725). Yet only the latter one is a positron emitter and is suitable for PET imaging while the two former ones are single photon emitters and used for SPECT. Also all of the above need a suitable chelating agent, which is typically linked to folic acid through its amino acid, i.e. glutamate portion.

Thus a folate radiopharmaceutical having a covalently linked positron emitting nuclide would be of great interest. In particular a $^{18}F$-labeled folate radiopharmaceutical would be most suitable for PET imaging because of its excellent imaging characteristics which would fulfill all of the above considerations. Compared with other suitable radionuclides ($^{11}C$, $^{13}N$, $^{15}O$), $^{18}F$ is very useful because of its longer half-life of approximately 110 minutes and because it decays by emitting positrons having a low positron energy of 635 keV, which allows a very high-resolution for PET images. Furthermore, the longer half-life of $^{18}F$ also allows for syntheses that are more complex and satellite distribution to PET centers with no cyclotron and/or no radiochemistry facilities. In addition the atomic radius of fluorine is comparable to that of H. This implies that steric effects of a fluorine-for-H substitution will hardly interfere with the binding of the ligand to the receptor. Only the high electronegativity of fluorine may influence the biochemical properties of a fluorinated ligand compared to the unsubstituted analogue.

Yet, the structure of folates does not lend itself to direct radiolabeling with $^{18}F$. Thus to date, there have been only very few $^{18}F$-labeled folates reported in the literature (Bettio et al., J. Nucl. Med., 2006, 47(7), 1153; WO 2006/071754). Moreover, these suggest $^{18}F$-labeling through conjugation at the glutamate portion of folates. To date there is no known $^{18}F$-labeled folate or derivative thereof, wherein the fluorine-18 is linked within the folate skeleton, such as to the benzoylamine moiety. In addition, the currently reported radiosynthesis was time-consuming and gave only low radiochemical yields of less than 5% (Bettio et al., J. Nucl. Med., 2006, 47(7), 1153) and thus is unsuitable for routine clinical applications.

Thus currently known $^{18}F$-labeled folates or derivatives thereof are not able to fill the need for specific radiopharmaceuticals suitable for metabolic imaging of tumors to improve diagnosis and treatment of cancer and inflammatory and autoimmune diseases.

Applicants have now found that $^{18}F$-labeled folate radiopharmaceuticals wherein the fluorine-18 is linked to the aminobenzoyl moiety within the folate skeleton may be obtained through for example direct radiolabeling.

Thus, the present invention is directed to new $^{18}F$-folate radiopharmaceuticals, wherein the fluorine-18 is covalently linked to the aminobenzoyl moiety which links the pteridine heterocycle to the amino acid portion within folate structures, as well as their precursors, a method of their preparation, preferably through direct radiolabeling, as well as their use in diagnosis and monitoring of cancer or inflammatory and autoimmune disease therapy.

SUMMARY OF THE INVENTION

The present invention is in a first aspect directed to new $^{18}F$-folate radiopharmaceuticals and precursors thereof (hereinafter also called compounds of the invention), wherein the fluorine-18 and/or at least one electron-withdrawing group is covalently linked to the aminobenzoyl moiety.

In one specific embodiment, the new folate radiopharmaceuticals are substituted with the fluorine-18 in the 2'- and/or 6'-position of the aminobenzoyl-moiety, optionally comprising at least one further electron-withdrawing group.

In a preferred embodiment the present invention is also directed towards 2'- and 6'-$^{18}F$-folate radiopharmaceuticals, optionally comprising at least one further electron-withdrawing group.

In another specific embodiment, the present invention is directed towards the precursors of the new folate radiopharmaceuticals. These include, for example, compounds that are substituted at the benzoyl moiety with at least one electron-withdrawing group which may act as a leaving group and is able to undergo nucleophilic aromatic substitution by [$^{18}F$]fluoride. Alternatively, the at least one electron-withdrawing group may act as an activator aiding the substitution by [$^{18}F$]fluoride. Preferred electron-withdrawing groups may include for example nitro, cyano, (trimethyl) ammonium, sulfonates, esters, ketones, chloro, bromo, fluoro, iodonium salts, dialkyl/-aryl silanes, silanols and the like.

In a further aspect the present invention is directed to a method of their preparation. In a preferred embodiment the $^{18}F$-folate radiopharmaceuticals of the invention are obtained through direct $^{18}F$-radiolabeling of suitable precursors.

In another aspect the present invention is directed to the use in diagnosis of a cell or population of cells expressing a folate-receptor and monitoring of cancer and cancer therapy in vitro or in vivo or monitoring of inflammatory and autoimmune diseases such rheumatoid arthritis and therapy thereof.

In one embodiment, the present invention is directed towards uses of $^{18}$F-folate radiopharmaceuticals of the invention for diagnostic imaging of a cell or population of cells expressing a folate-receptor.

More specifically the present invention includes methods for diagnostic imaging of a cell or population of cells expressing a folate-receptor, which includes for example methods for in vitro detection of a cell expressing the folate receptor, for example a tumor cell or an activated macrophage, in a tissue sample. Such methods may also be performed in vivo.

Thus, in a further embodiment the present invention is directed towards uses of $^{18}$F-folate radiopharmaceuticals of the invention for convenient and effective administration to a subject in need for diagnostic imaging and/or monitoring of cancer or inflammatory and autoimmune disease therapy. The subject of the methods of the present invention is preferably a mammal, such as an animal or a human, preferably a human.

Such methods of the invention may be performed in combination with any other methods of diagnosis or therapy of cancer or inflammatory and autoimmune diseases including methods using other already developed diagnostic and/or therapeutic agents and utilizing x-ray computed tomography (CT), magnetic resonance imaging (MRI), functional magnetic resonance imaging (fMRI), single photon emission computed tomography (SPECT), optical imaging, and ultrasound.

Other features and advantages of the invention will be apparent from the following detailed description thereof and from the claims.

BRIEF DESCRIPTION OF FIGURES THE DRAWINGS

FIG. 1. Data from ex vivo biodistribution studies using 2'-[$^{18}$F]fluoro-folic acid: specific uptake in folate receptor-positive tissues.

FIG. 2. PET images using 2'-[$^{18}$F]fluoro-folic acid (the arrows indicate the position of the KB xenografts tumors).

FIG. 3. PET images using 2'-[$^{18}$F]fluoro-folic acid (the arrows indicate the kidneys).

FIG. 4. Ex vivo PET images of KB xenografts tumors using 2'-[$^{18}$F]fluoro-folic acid.

DETAILED DESCRIPTION OF THE INVENTION

The present invention is in a first aspect directed to new $^{18}$F-folate radiopharmaceuticals and precursors thereof (hereinafter also called compounds of the invention), wherein the fluorine-18 and/or at least one electron-withdrawing group is covalently linked to the aminobenzoyl moiety.

$^{18}$F is usually available as electrophilic [$^{18}$F]F$_2$ and as generally used herein, as nucleophilic [$^{18}$F]fluoride. In form of [$^{18}$F]fluoride fluorine-18 is producible more efficiently. In addition, this is the only possibility for preparing no carrier added radiotracers sufficiently.

In a preferred embodiment a folate (structure) or derivative thereof, also hereinafter simply referred to as "a folate" or "folates", for use in the present invention comprises compounds based on a condensed pyrimidine heterocycle, which is linked to an aminobenzoyl moiety carrying in para-position an amino acid portion. As used herein a "condensed pyrimidine heterocycle" includes a pyrimidine fused with a further 5- or 6-membered heterocycle, such as a pteridine or a pyrrolopyrimidine bicycle. As used herein the term "amino acid" includes compounds with both an amino group (e.g., NH$_2$ or NH$_3^+$) and a carboxylic acid group (e.g., COOH or COO). In a specific embodiment, the amino acid may be an α-amino acid, a β-amino acid, a D-amino acid or an L-amino acid. The amino acid may be a naturally occurring amino acid (e.g., alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine, or histidine, etc.) or it may be a derivative thereof. Examples of derivatives include optionally substituted amino acids, e.g. having one or more substituents selected from CN, Hal, and/or NO$_2$ (e.g. fluoroglutamic acid). The amino acid may also include any other non-naturally occurring amino acids, such as e.g. norleucine, norvaline, L- or D-naphthalanine, ornithine, homoarginine and others well known in the peptide art (see for example in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference). Amino acids and amino acid analogs/derivatives can be purchased commercially (Sigma Chemical Co.; Advanced Chemtech) or synthesized using methods known in the art. In another specific embodiment, the amino acid may also be part of a polyamino acid (also termed polypeptide), wherein a plurality of same or different amino acids as defined hereinabove are covalently linked, i.e. linked through conventional peptide or other bonds. Preferred amino acids include for example glutamic acid, aspartic acid, glutamine, aspartine, lysine, arginine, cystein, and derivatives thereof and preferred polyamino acids include homopolymers the respective homopolymers thereof (i.e. polyglutamic acid, polyaspartic acid, etc). Most preferred are optionally substituted aspartic and glutamic acid.

Preferred representatives of folates as used herein are based on a folate skeleton, i.e. pteroyl-glutamic acid or N-[4(pteridin-6-ylmethylamino)benzoyl]-glutamic acid), and derivatives thereof and includes optionally substituted folic acid, folinic acid, pteropolyglutamic acid, and folate receptor-binding pteridines such as tetrahydropterins, dihydrofolates, tetrahydrofolates, and their deaza and dideaza analogs. Folic acid is the preferred basic structure used for the compounds of this invention. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5-dideaza, 5,10-dideaza, 8,10-dideaza, and 5,8-dideaza analogs. Preferred deaza analogs compounds include N-[4-[2-[(6R)-2-amino-1,4,5,6,7,8-hexahydro-4-oxopyrido[2,3-d]pyrimidin-6-yl]ethyl]benzoyl]-L-glutamic acid (Lometrexol) and N-[4-[1-[(2,4-diamino-6-pteridinyl) methyl]propyl]benzoyl]-L-glutamic acid (Edatrexate).

In a particular embodiment, the new folate radiopharmaceuticals are labeled with the fluorine-18 in the 2'-, 3'-, 5'- or 6'-position of the aminobenzoyl-moiety, preferably in the 2'- or 6'-position. Most preferred are 2'- and 6'-$^{18}$F-folate folate radiopharmaceuticals. Optionally the new folate radiopharmaceuticals further comprise at least one electron-withdrawing group.

In another particular embodiment the present invention is directed towards the precursors of these new folate radiopharmaceuticals, wherein the aminobenzoyl moiety is substituted with at least one electron-withdrawing group, preferably selected from —NO₂, —CN, —N⁺(CH₃)₃, —SO₃R', —COOR', —COR', —Cl, —Br, —F, iodonium salts —I⁺(R')₂, dialkyl/-aryl silanes —SiOH(R')₂, and silanols —SiH(R')₂, wherein R' is independently a straight-chain or branched $C_{(1-12)}$ alkyl group or an optionally substituted carbocyclic and heterocyclic group comprising five-, six- or ten-membered ring systems most preferably one or two electron-withdrawing groups in the 2'- and/or 6'-position of the aminobenzoyl moiety.

Thus in a specific embodiment the present invention is directed towards compounds of formula I,

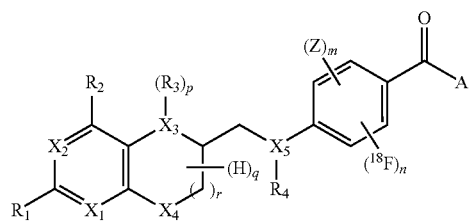

wherein
A is an amino acid,
$X_1$ to $X_5$ are independently of each other N or C,
$X_6$, $X_7$ are independently of each other C, N or O,
Z is an electron-withdrawing group preferably selected from —NO₂, —CN, —N⁺(CH₃)₃, —SO₃R', —COOR', —COR', —Cl, —Br, —F, iodonium salts —I⁺(R')₂, dialkyl/-aryl silanes —SiOH(R')₂, and silanols —SiHR(")₂, wherein R' is independently a straight-chain or branched $C_{(1-12)}$ alkyl group or an optionally substituted carbocyclic and heterocyclic group comprising five-, six- or ten-membered ring systems,
$R_1$, $R_2$ are independently of each other H, Hal, —OR", —NHR", C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein R" is H or C1-C6 alkyl,
$R_3$, $R_4$ are independently of each other H, formyl, iminomethyl, nitroso, C1-C12 alkyl, C1-C12 alkoxy, C1-C12 alkanoyl, halosubstituted C1-C12 alkanoyl,
$R_5$, $R_6$ are independently of each other H or straight chain or branched $C_1$-$C_{12}$ alkyl, which is unsubstituted or substituted by at least one CN, Hal, or NO₂, and wherein one or more of embedded, non-adjacent CH2 groups may independently be replaced by —O—, —CO—, —CO—O—, —CO—NR'—, —CH=CH—, —C≡C—,
m is 0, 1, 2 or 3,
n is 0 or 1,
p is 0, 1 or 2,
q has a value of 1 to 7, and
r is 0 or 1.

In a specific embodiment A is an amino acid selected from glutamic acid, aspartic acid, glutamine, aspartine, lysine, arginine, cystein, and derivatives thereof or a polyamino acid selected from the respective homopolymers. In a preferred embodiment A is optionally substituted aspartic acid, glutamic acid, polyaspartic acid or polyglutamic acid.

Thus the present invention is further directed towards compounds of formula I wherein A is e.g. a glutamic acid residue, having formula II,

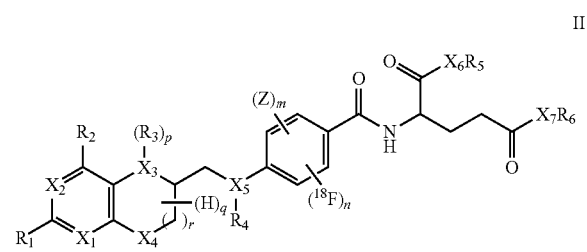

wherein
$X_1$ to $X_5$ are independently of each other N or C,
$X_6$, $X_7$ are independently of each other C, N or O,
Z is an electron-withdrawing group preferably selected from —NO₂, —CN, —N⁺(CH₃)₃, —SO₃R', —COOR', —COR', —Cl, —Br, —F, iodonium salts —I⁺(R')₂, dialkyl/-aryl silanes —SiOH(R')₂, and silanols —SiHR(")₂, wherein R' is independently a straight-chain or branched $C_{(1-12)}$ alkyl group or an optionally substituted carbocyclic and heterocyclic group comprising five-, six- or ten-membered ring systems,
$R_1$, $R_2$ are independently of each other H, Hal, —OR", —NHR", C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein R" is H or C1-C6 alkyl,
$R_3$, $R_4$ are independently of each other H, formyl, iminomethyl, nitroso, C1-C12 alkyl, C1-C12 alkoxy, C1-C12 alkanoyl, halosubstituted C1-C12 alkanoyl,
$R_5$, $R_6$ are independently of each other H or straight chain or branched $C_1$-$C_{12}$ alkyl, which is unsubstituted or substituted by at least one CN, Hal, or NO₂, and wherein one or more of embedded, non-adjacent CH2 groups may independently be replaced by —O—, —CO—, —CO—O—, —CO—NR'—, —CH=CH—, —C≡C—,
m is 0, 1, 2 or 3,
n is 0 or 1,
p is 0, 1 or 2,
q has a value of 1 to 7, and
r is 0 or 1.

In a preferred embodiment the fluorine-18 is at the 2'- or 6'-position.

In another preferred embodiment
R' is H, $C_1$-$C_6$ alkyl, $C_1$-$C_6$ alkoxy, $C_1$-$C_6$ alkanoyl, $C_2$-$C_6$ alkenyl, $C_2$-$C_6$ alkynyl, ($C_1$-$C_6$ alkoxy)carbonyl, or ($C_{1-6}$ alkylamino)carbonyl.

In a further preferred embodiment
$R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, and
$R_5$, $R_6$ are independently of each other H or straight chain or branched $C_1$-$C_{12}$ alkyl, which is unsubstituted or substituted by at least one CN, Hal, or NO₂, and wherein one or more of embedded, non-adjacent CH2 groups may independently be replaced by —O—, —CO—, —CO—O—, —CO—NR'—, —CH=CH—, —C≡C—.

In an even more preferred embodiment
R' is H, methyl- or ethyl-,
$R_3$, $R_4$ are independently of each other H, methyl- or formyl-, and $R_5$, $R_6$ are independently of each other H, methyl-, ethyl- or tert.-butyl-.

More preferred are thus compounds of formulae III or IV,

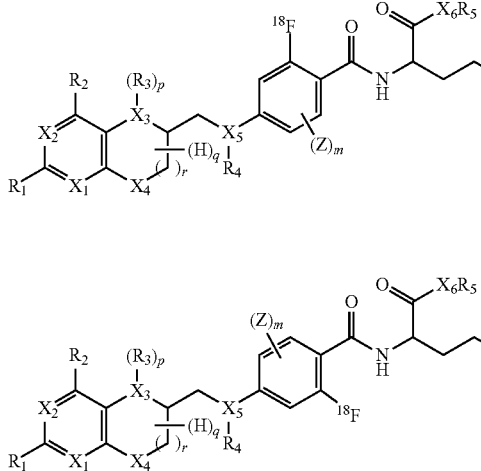

III

IV wherein $X_1$ to $X_5$ are independently of each other N or C, $X_6$, $X_7$ are independently of each other C, N or O, Z is an electron-withdrawing group preferably selected from —$NO_2$, —CN, —$N^+(CH_3)_3$, —$SO_3R'$, —COOR', —COR', —Cl, —Br, —F, iodonium salts —$I^+(R')_2$, dialkyl/-aryl silanes —$SiOH(R')_2$, and silanols —SiH $(R')_2$, wherein R' is independently a straight-chain or branched $C_{(1-12)}$ alkyl group or an optionally substituted carbocyclic and heterocyclic group comprising five-, six- or ten-membered ring systems, $R_1$, $R_2$ are independently of each other H, Hal, —OR", —NHR", C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein R" is H or C1-C6 alkyl, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, $R_5$, $R_6$ are independently of each other H or straight chain or branched $C_1$-$C_{12}$ alkyl, which is unsubstituted or substituted by at least one CN, Hal, or $NO_2$, and wherein one or more of embedded, non-adjacent CH2 groups may independently be replaced by —O—, —CO—, —CO—O—, —CO—NR'—, —CH=CH—, —C≡C—, m is 0, 1, 2, or 3, p is 0, 1 or 2, q has a value of 1 to 7, and r is 0 or 1.

Preferred embodiments of compounds of formula I also apply to compounds of formulae III and IV.

Further preferred compounds are compounds of formulae I, II, III or IV, wherein m=0. Thus, in another preferred embodiment, the present invention is directed towards compounds of formulae V and VI

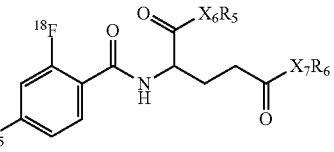

V

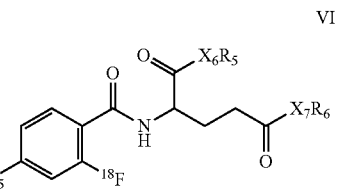

VI wherein $X_1$ to $X_5$ are independently of each other N or C, $X_6$, $X_7$ are independently of each other C, N or O, $R_1$, $R_2$ are independently of each other H, Hal, —OR", —NHR", C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein R" is H or C1-C6 alkyl, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, $R_5$, $R_6$ are independently of each other H or straight chain or branched $C_1$-$C_{12}$ alkyl, which is unsubstituted or substituted by at least one CN, Hal, or $NO_2$, and wherein one or more of embedded, non-adjacent CH2 groups may independently be replaced by —O—, —CO—, —CO—O—, —CO—NR'—, —CH=CH—, —C≡C—, p is 0, 1 or 2, q has a value of 1 to 7, and r is 0 or 1.

Preferred embodiments of compounds of formulae I to IV also apply to compounds of formulae V and VI.

In another specific embodiment, the present invention is directed towards compounds of formula I wherein m is 1 or 2, such that more preferably the electron-withdrawing group(s) Z is at the 2'- and/or 6'-position.

More preferred are thus compounds of formulae VII, VIII, IX, X and XI,

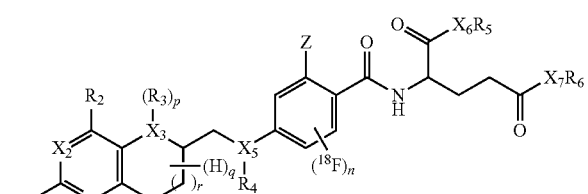

VII

-continued

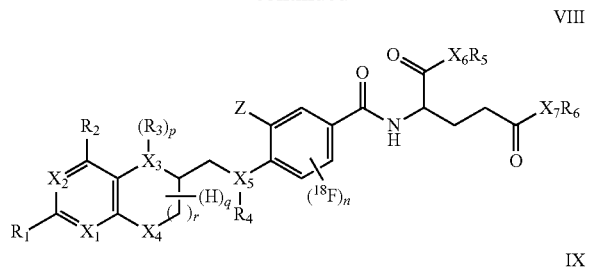

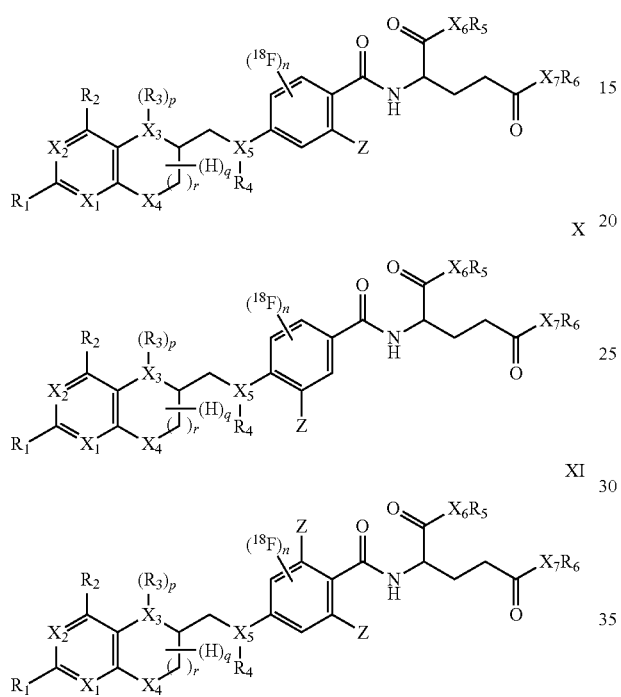

wherein
- $X_1$ to $X_5$ are independently of each other N or C,
- $X_6$, $X_7$ are independently of each other C, N or O,
- Z is a electron-withdrawing group preferably selected from —$NO_2$, —CN, —$N^+(CH_3)_3$, —$SO_3R'$, —COOR', —COR', —Cl, —Br, —F, iodonium salts —$I^+(R')_2$, dialkyl/-aryl silanes —$SiOH(R')_2$, and silanols —$SiH(R')_2$, wherein R' is independently a straight-chain or branched $C_{(1-12)}$ alkyl group or an optionally substituted carbocyclic and heterocyclic group comprising five-, six- or ten-membered ring systems,
- $R_1$, $R_2$ are independently of each other H, Hal, —OR", —NHR", C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein R" is H or C1-C6 alkyl,
- $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl,
- $R_5$, $R_6$ are independently of each other H or straight chain or branched $C_1$-$C_{12}$ alkyl, which is unsubstituted or substituted by at least one CN, Hal, or $NO_2$, and wherein one or more of embedded, non-adjacent CH2 groups may independently be replaced by —O—, —CO—, —CO—O—, —CO—NR'—, —CH=CH—, —C≡C—,

- n is 0 or 1,
- p is 0 or 1,
- q has a value of 1 to 7, and
- r is 0 or 1.

Preferred embodiments of compounds of formulae I to VI also apply to compounds of formulae VII, VIII, IX, X and XI.

Further preferred compounds are compounds of formulae I, VII, VIII, IX, X or XI, wherein n=0. Thus, in another preferred embodiment, the present invention is directed towards compounds of formulae XII, XIII and XIV

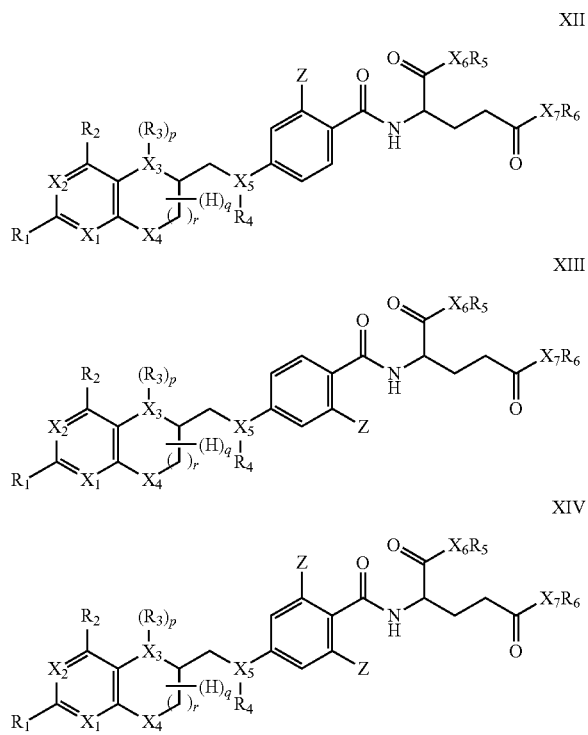

wherein
- $X_1$ to $X_5$ are independently of each other N or C,
- $X_6$, $X_7$ are independently of each other C, N or O,
- Z is an electron-withdrawing group preferably selected from —$NO_2$, —CN, —$N^+(CH_3)_3$, —$SO_3R'$, —COOR', —COR', —Cl, —Br, —F, iodonium salts —$I^+(R')_2$, dialkyl/-aryl silanes —$SiOH(R')_2$, and silanols —$SiH(R')_2$, wherein R' is independently a straight-chain or branched $C_{(1-12)}$ alkyl group or an optionally substituted carbocyclic and heterocyclic group comprising five-, six- or ten-membered ring systems,
- $R_1$, $R_2$ are independently of each other H, Hal, —OR", —NHR", C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein R" is H or C1-C6 alkyl,
- $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl,
- $R_5$, $R_6$ are independently of each other H or straight chain or branched $C_1$-$C_{12}$ alkyl, which is unsubstituted or substituted by at least one CN, Hal, or $NO_2$, and wherein one or more of embedded, non-adjacent CH2 groups may independently be replaced by —O—, —CO—, —CO—O—, —CO—NR'—, —CH=CH—, —C≡C—, p is 0, 1 or 2, q has a value of 1 to 7, and r is 0 or 1.

Preferred embodiments of compounds of formulae I to XI also apply to compounds of formulae XII, XIII and XIV.

It is understood, that the abbreviations "N" and "C" are representative for all possible degrees of saturation, i.e. N includes —NH— and —N═ linkages and C includes —CH$_2$— and —CH═ linkages.

It is further understood, that (H)$_q$ represents all H substituents on the indicated ring (i.e. on X$_3$, C6, C7 and X$_4$). For example q=5 for a fully saturated unsubstituted analog (X$_3$=X$_4$=N, p=0) or q=7 for a fully saturated unsubstituted 5,8-dideaza analog (X$_3$=X$_4$=C, p=0) and q=1 for a fully unsaturated analog with X$_3$=X$_4$=N, p=0.

A preferred embodiment of compounds of formulae I to XIV includes for example wherein X$_1$ to X$_5$ are N, R$_1$ is NY$_4$Y$_5$, R$_2$ is O, p is 0 and q is 1.

Thus, in a further specific embodiment the present invention is directed to a compound of formula XV,

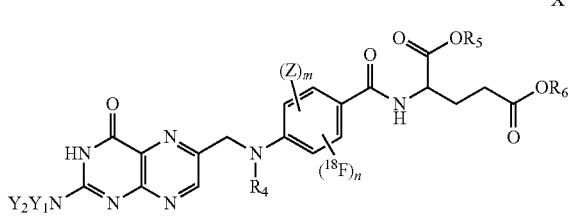

XV wherein

Z is an electron-withdrawing group preferably selected from —NO$_2$, —CN, —N$^+$(CH$_3$)$_3$, —SO$_3$R', —COOR', —COR', —Cl, —Br, —F, iodonium salts —I$^+$(R')$_2$, dialkyl/-aryl silanes —SiOH(R')$_2$, and silanols —SiH(R')$_2$, wherein R' is independently a straight-chain or branched C$_{(1-12)}$ alkyl group or an optionally substituted carbocyclic and heterocyclic group comprising five-, six- or ten-membered ring systems, R$_5$, R$_6$, are independently of each other H or straight chain or branched C$_1$-C$_{12}$ alkyl, which is unsubstituted or substituted by at least one CN, Hal, or NO$_2$, and wherein one or more of embedded, non-adjacent CH2 groups may independently be replaced by —O—, —CO—, —CO—O—, —CO—NR'—, —CH═CH—, —C≡C—, Y$_1$, Y$_2$ are independently of each other selected from H, formyl, straight chain or branched C$_1$-C$_{12}$ alkyl, which is unsubstituted or substituted by at least one CN, Hal, or NO$_2$, and wherein one or more of embedded, non-adjacent CH2 groups may independently be replaced by —O—, —CO—, —CO—O—, —CO—NR'—, —CH═CH—, —C≡C—, R$_4$ is selected from H, nitroso, C$_1$-C$_{12}$ alkyl, C$_1$-C$_{12}$ alkoxy, C$_1$-C$_{12}$ alkanoyl, halosubstituted C$_1$-C$_{12}$ alkanoyl, m is 0, 1, 2 or 3, and n is 0 or 1.

Preferred embodiments of compounds of formulae I to XIV also apply to compounds of formula XV.

Thus, in a further specific embodiment the present invention is directed to a compound of formula XVI,

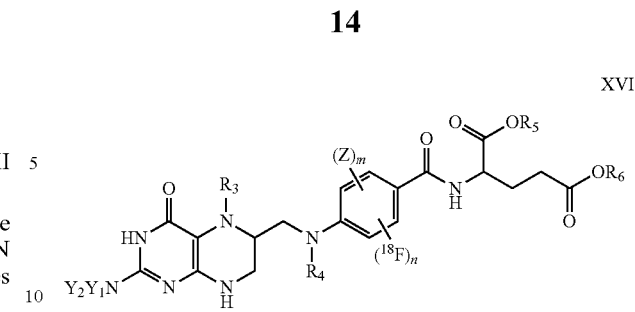

XVI wherein

Z is an electron-withdrawing group preferably selected from —NO$_2$, —CN, —N$^+$(CH$_3$)$_3$, —SO$_3$R', —COOR', —COR', —Cl, —Br, —F, iodonium salts —I$^+$(R')$_2$, dialkyl/-aryl silanes —SiOH(R')$_2$, and silanols —SiH(R')$_2$, wherein R' is independently a straight-chain or branched C$_{(1-12)}$ alkyl group or an optionally substituted carbocyclic and heterocyclic group comprising five-, six- or ten-membered ring systems, R$_3$, R$_4$ are independently of each other H, formyl, iminomethyl, nitroso, C1-C12 alkyl, C1-C12 alkoxy, C1-C12 alkanoyl, halosubstituted C1-C12 alkanoyl, R$_5$, R$_6$ are independently of each other H or straight chain or branched C$_1$-C$_{12}$ alkyl, which is unsubstituted or substituted by at least one CN, Hal, or NO$_2$, and wherein one or more of embedded, non-adjacent CH2 groups may independently be replaced by —O—, —CO—, —CO—O—, —CO—NR'—, —CH═CH—, —C≡C—, Y$_1$, Y$_2$ are independently of each other selected from H, formyl, straight chain or branched C$_1$-C$_{12}$ alkyl, which is unsubstituted or substituted by at least one CN, Hal, or NO$_2$, and wherein one or more of embedded, non-adjacent CH2 groups may independently be replaced by —O—, —CO—, —CO—O—, —CO—NR'—, —CH═CH—, —C≡C—, m is 0, 1, 2 or 3, and n is 0 or 1.

Preferred embodiments of compounds of formulae I to XV also apply to compounds of formula XVI.

Other embodiments are compounds of formulae I to XIV wherein X$_1$ to X$_5$ and R$_1$ and R$_2$ are N, R$_3$=R$_5$=R$_6$ is H, R$_4$ is CH$_3$, p is 0 and q is 1.

Thus, in a further specific embodiment the present invention is directed to a compound of formula XVII,

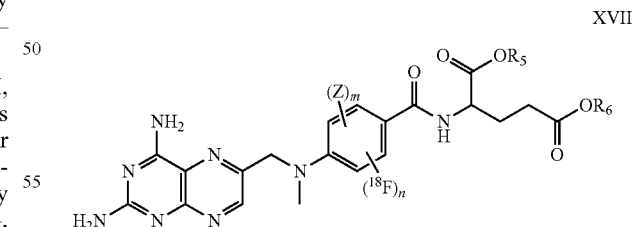

XVII wherein

Z is an electron-withdrawing group preferably selected from —NO$_2$, —CN, —N$^+$(CH$_3$)$_3$, —SO$_3$R', —COOR', —COR', —Cl, —Br, —F, iodonium salts —I$^+$(R')$_2$, dialkyl/-aryl silanes —SiOH(R')$_2$, and silanols —SiH(R')$_2$, wherein R' is independently a straight-chain or branched C$_{(1-12)}$ alkyl group or an optionally substituted carbocyclic and heterocyclic group comprising five-, six- or ten-membered ring systems, $R_5$, $R_6$ are independently of each other H or straight chain or branched $C_1$-$C_{12}$ alkyl, which is unsubstituted or substituted by at least one CN, Hal, or $NO_2$, and wherein one or more of embedded, non-adjacent CH2 groups may independently be replaced by —O—, —CO—, —CO—O—, —CO—NR'—, —CH=CH—, —C≡C—, m is 0, 1, 2 or 3, and n is 0 or 1.

Other embodiments are compounds of formulae I to XIV wherein $X_1$ to $X_5$ and $R_1$ and $R_2$ are N, $R_4$=$R_5$=$R_6$ is H, $R_3$ is $CH_3$ or formyl, p is 1 and q is 4.

Thus, in a further specific embodiment the present invention is directed to a compound of formula XVIII,

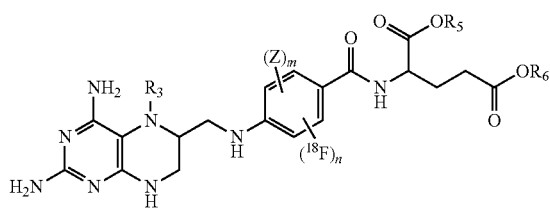

XVIII wherein

Z is an electron-withdrawing group preferably selected from —$NO_2$, —CN, —$N^+(CH_3)_3$, —$SO_3R'$, —COOR', —COR', —Cl, —Br, —F, iodonium salts —$I^+(R')_2$, dialkyl/-aryl silanes —$SiOH(R')_2$, and silanols —SiH$(R')_2$, wherein R' is independently a straight-chain or branched $C_{(1-12)}$ alkyl group or an optionally substituted carbocyclic and heterocyclic group comprising five-, six- or ten-membered ring systems, $R_3$ is H, methyl- or formyl-, $R_5$, $R_6$ are independently of each other H or straight chain or branched $C_1$-$C_{12}$ alkyl, which is unsubstituted or substituted by at least one CN, Hal, or $NO_2$, and wherein one or more of embedded, non-adjacent CH2 groups may independently be replaced by —O—, —CO—, —CO—O—, —CO—NR'—, —CH=CH—, —C≡C—, m is 0, 1, 2 or 3, and n is 0 or 1.

The term "alkyl", when used singly or in combination, refers to straight chain or branched alkyl groups typically containing 1 to 12, preferably 1 to 8 more preferably 1 to 4 carbon atoms, such as methyl, ethyl, propyl, isopropyl, butyl, sec-butyl, isobutyl, t-butyl, pentyl isopentyl, neopentyl, hexyl and the like.

As used herein, the term "alkenyl" (i.e. an alkyl group as defined above having at least one double bond), singly or in combination with other groups, refers to straight chain or branched alkylene groups containing 2 to 12 carbon atoms, such as methylene, ethylene, propylene, isopropylene, butylene, t-butylene, sec-butylene, isobutylene, amylene, isoamylene, pentylene, isopentylene, hexylene and the like. The preferred alkenyl groups contain 2 to 8 carbon atoms.

The term "alkynyl" (i.e. an alkyl group as defined above having at least one triple bond) as used herein refers to a linear or branched chain of carbon atoms with one or more carbon-carbon triple bonds. The preferred alkynyl groups contain 2 to 12, more preferably 2 to 8 carbon atoms.

The term "alkoxy" as used herein refers to an alkyl, as defined above, substituted with oxygen, such as methoxy, ethoxy, propoxy, isopropoxy, butoxy, tert-butoxy and the like.

The term "alkanoyl" as used herein refers to formyl, or an alkyl, as defined above, terminally-substituted with a carbonyl such as acetyl, propanoyl, butanoyl, pentanoyl and the like.

The term "alkylamino" as used herein refers to an alkyl, as defined above, substituted with nitrogen, including both monoalkylamino such as methylamino, ethylamino, propylamino, tertbutylamino, and the like, and dialkylamino such as dimethylamino, diethylamino, methylpropylamino, and the like.

The term "halo" as used herein refers to any Group 17 element and includes fluoro, chloro, bromo, iodo, and astatine(o).

The expression "optionally substituted" preferably includes substitution with hydroxy, alkoxy, (di)alkylamino, alkylsulfonyl, alkylcarbonyl, alkylcarbonyloxy, alkoxycarbonyl, carboxyl, Hal, CN, $NO_2$.

The expression "carbocyclic and heterocyclic group comprising five-, six- or ten-membered ring systems and the like" preferably includes phenyl, naphthyl, azetidinyl, pyrrolidinyl, imidazolyl, indolyl, oxadiazolyl, thiadiazolyl, triazolyl, tetrazolyl, oxatriazolyl, thiatriazolyl, pyridazinyl, morpholinyl, pyrimidinyl, pyrazinyl, pyridyl, quinolinyl, isoquinolinyl, piperidinyl, pyrazolyl, imidazopyridinyl and piperazinyl, more preferably phenyl, naphthyl, pyrrolidinyl, imidazolyl, triazolyl, pyrimidinyl, pyridyl, piperidinyl, and pyrazolyl, most preferably phenyl, pyridyl and naphthyl.

The term "electron-withdrawing group" or "group Z" as used herein refers to a functionality, which can act as a leaving group and thus can be exchanged by an incoming [$^{18}$F]fluoride or else can act as an activator for the introduction of the [$^{18}$F]fluoride. Suitable electron-withdrawing groups include —$NO_2$, —CN, —$N^+(CH_3)_3$, —$SO_3R'$, —COOR', —COR', —Cl, —Br, —F, iodonium salts —$I^+(R')_2$, dialkyl/-aryl silanes —$SiOH(R')_2$, and silanols —SiH$(R')_2$, wherein R' is independently a straight-chain or branched $C_{(1-12)}$ alkyl group or an optionally substituted carbocyclic and heterocyclic group comprising five-, six- or ten-membered ring systems and the like, preferably —$NO_2$, —CN, —$N^+(CH_3)_3$, —$SO_3R'$, —COOR', —COR', —Cl, —Br, —F, more preferably —$NO_2$, —CN, —$N^+(CH_3)_3$.

In a preferred embodiment $R_1$ and $R_2$ are independently of each other H, —OR", —NHR" wherein R" is H, $C_1$-$C_6$ alkyl, $C_1$-$C_4$ alkoxy, $C_1$-$C_4$ alkanoyl, ($C_1$-$C_4$ alkoxy)carbonyl, and ($C_1$-$C_6$ alkylamino)carbonyl, more preferably $R_1$ and $R_2$ are independently of each other —OH, $NH_2$.

In a preferred embodiment $R_3$ and $R_4$ are independently of each other H, methyl or formyl.

In a preferred embodiment $R_5$ and $R_6$ are independently of each other H, methyl, ethyl or tert.-butyl.

In a preferred embodiment R' is H, methyl or ethyl.

In a preferred embodiment R" is H, methyl or ethyl.

In a further aspect the present invention provides a method of synthesizing a compound of the invention. Applicants have found that the folate radiopharmaceuticals of the invention may be obtained through direct radiolabeling with [$^{18}$F]fluoride.

More specifically, a method of production of the invention comprises the steps of providing a precursor having formula I wherein n=0 and reacting said precursor with [$^{18}$F]fluoride activated by phase transfer catalysts such as tetrabutylammonium carbonate or aminopolyethers (e.g. Kryptofix© 2.2.2) in combination with potassium carbonate or oxalate to form a compound having formula I including a [$^{18}$F]fluoro group. In a preferred embodiment the folate radiopharmaceuticals were obtained in a direct labeling method based on a fluoro-for-nitro-exchange.

In a typical reaction, a suitable organic solvent was added to dry $^{18}$F-Fluoride-cryptate and the resulting solution was added to a suitably protected precursor, which was provided in a sealed reaction vessel with a base such as DIEA, TEA or pyridine. The resulting mixture was heated to 140-145° C. for 20-25 min. After short cartridge purification, deprotection was carried out under basic or acidic conditions and a gentle heating for 5-10 min. Crude product solution was neutralized and injected to semi-prep HPLC system. The radioactive product was collected and the HPLC solvents removed by a stream of nitrogen, vacuum and gentle heating. For the formulation, the dry product was redissolved with physiological solution and transferred to sterile vial using a sterile filter.

In a further aspect the present invention provides uses of folate radiopharmaceuticals of the invention for convenient and effective administration to a subject in need for diagnostic imaging.

Thus the present invention provides a method for diagnostic imaging of a cell or population of cells expressing a folate-receptor, said method comprising the steps of administering at least one folate radiopharmaceutical of the invention in a diagnostic imaging amount, and obtaining a diagnostic image of said cell or population of cells.

Such imaging may be performed on a cell or population of cells expressing a folate-receptor in vitro or in vivo.

Thus, the present invention provides a method for in vitro detection of a cell expressing the folate receptor in a tissue sample which includes contacting said tissue sample with at least one folate radiopharmaceutical of the invention in effective amounts and for sufficient time and conditions to allow binding to occur and detecting such binding by imaging techniques such as autoradiography and the like.

In a further aspect the present invention provides uses of folate radiopharmaceuticals of the present invention for convenient and effective administration to a subject in need for diagnostic imaging or monitoring of cancer or inflammatory and autoimmune disease therapy.

In another aspect the present invention provides a method for simultaneous diagnosis and therapy, comprising the steps of administering to a subject in need thereof at least one folate radiopharmaceutical of the present invention in a diagnostically effective amount in combination with a therapeutically active, and obtaining a diagnostic image of said tissues to follow the course of treatment.

The subject of the methods of the present invention is preferably a mammal, such as an animal or a human, preferably a human.

The dosage depends on the nature of the effect desired, such as the form of diagnosis or therapy, on the kind and frequency of treatment, on the diagnostic instrumentation, on the form of application of the preparation, and on the age, weight, nutrition and condition of the recipient, kind of concurrent treatment, if any.

However, the most preferred dosage can be tailored to the individual subject, as is understood and determinable by one of skill in the art, without undue experimentation. This typically involves adjustment of a standard dose, e.g., reduction of the dose if the patient has a low body weight.

Treatment can commence with a smaller amount, below the optimum amount, which can be increased in order to achieve the optimum effect.

The folate radiopharmaceuticals of the present invention may be administered either as a repeated dose or preferably as a single dose. For example, the folate radiopharmaceuticals of this invention may be administered to a subject by intravenous bolus injection. The suitable forms for injection include sterile aqueous solutions or dispersions of the above mentioned folate radiopharmaceuticals of the present invention.

For a solution to be injected a preferred unit dosage is from about 0.01 mL to about 10 mL. After e.g. intravenous administration, imaging of the organ or tumor in vivo can take place, if desired, from 30 min to 4 hours, after the radiolabeled reagent has been administered to a subject. Typically, a sufficient amount of the administered dose will accumulate in the targeted area.

The folate radiopharmaceuticals are preferably purified by HPLC. After removing the solvents of the HPLC purification the products were preferably solved in physiological solutions such as 0.9% NaCl or 0.15M phosphate buffer solution, before the application, the formulated radiopharmaceutical is transferred to a sterile vial via a sterile filter.

The folate radiopharmaceuticals of the invention may also be used for in vitro detection of a cell expressing the folate receptor in a tissue biopsy taken from a subject. Thus in a further embodiment the present invention provides a method for in vitro detection of a cell expressing the folate receptor, e.g. a tumor cell or an activated macrophage, in a tissue sample which includes contacting said tissue sample with a folate radiopharmaceutical of the present invention in effective amounts and for sufficient time and conditions to allow binding to occur and detecting such binding by imaging techniques.

Samples can be collected by procedures known to the skilled person, e.g., by collecting a tissue biopsy or a body fluid, by aspirating for tracheal or pulmonary samples and the like.

Tissue samples to be tested include any tissue suspected to contain a cell expressing a folate receptor, such as tumor cells, epithelial cells, kidneys, gastrointestinal or the hepatobiliary system, activated macrophages, monocytes, and others. Samples can be sectioned, e.g., with a microtome, to facilitate microscopic examination and observation. Samples can also be fixed with an appropriate fixative either before or after incubation with one of the folate radiopharmaceuticals of the present invention to improve the histological quality of sample tissues.

Time and conditions sufficient for binding of a folate radiopharmaceutical of the present invention to a folate receptor on the cell include standard tissue culture conditions, i.e. samples can be cultured in vitro and incubated with one of the compounds or compositions of the present invention in physiological media. Such conditions are well known to the skilled person. Alternatively, samples can be fixed and then incubated with a folate radiopharmaceutical of the present invention in an isotonic or physiological buffer.

For all applications it is convenient to prepare the compounds or compositions of the present invention at, or near, the site where they are to be used.

All of the compounds and/or methods disclosed and claimed herein can be made and executed without undue experimentation in light of the present disclosure. It will be apparent to those of skill in the art that variations may be applied to the present invention without departing from the scope of the invention. The Examples provided herein are intended to be illustrative and are not exhaustive; therefore the illustrated Examples should not be viewed as limiting the invention in any way.

EXAMPLES

Materials and Methods

Production of [$^{18}$F]fluoride n.c.a. [$^{18}$F]fluoride was produced via the $^{18}$O (p,n)$^{18}$F nuclear reaction at a Cyclone 18/9 cyclotron (IBA, Belgium). Isotopically 97% enriched [$^{18}$O]water was irradiated by a 16 MeV proton beam using a 2.1 ml liquid target. The [$^{18}$F]fluoride/[$^{18}$O]water solution was transferred from the target to a manipulator equipped syntheses hotcell using a helium stream. [$^{18}$F]fluoride (~20-30 GBq) was trapped on an anion exchange cartridge (Sep-Pak® Light Accell Plus QMA, Waters AG), preconditioned with 5 ml 0.5M potassium carbonate solution and 5 ml water, while the [$^{18}$O]water was recovered for recycling. $^1$H-NMR-spectra: $^1$H-NMR-spectra were recorded on a Varian Mercury Plus 200 (200 MHz) spectrometer. Chemical shifts were reported using TMS (Tetramethylsilan) as an internal standard. The electron spray ionisation mass spectra were recorded on an Agilent XCT spectrometer.

HPLC: For HPLC analysis of the precursors and the 2'-fluorofolic acid the following HPLC method was used: eluent A was aq. 0.05 M $NaH_2PO_4$ which was adjusted to pH 7.0 by addition of 32% aq. sodium hydroxide solution. Eluent B was a 1:1 mixture of solvent A and methanol. The column used was RP 18, Nucelosil, the gradient was from 100% eluent A to 100% eluent B within 30 min., 20 mg of the sample were dissolved in a buffer consisting of 20 g $NaHCO_3$ and 20 g $KHCO_3$ in 1000 ml of water.

For all other intermediates the following HPLC method was used: Same method as described above, but eluent B was composed of 800 ml methanol and 200 ml 0.05 M $NaH_2PO_4$.

For semi-preparative HPLC purification of the 2'[$^{18}$F] fluorofolic acid was carried out on a RP 18 column, Gemini 5μ C18, 250×10 mm, using a gradient as follows. Solvent A=0.05M phosphate buffer solution, B=methanol, 0-30 min: A: 99%→40%, 30-40 min: A: 40%→10%, 40-45 min: A: 40%→99%.

Example 1: Synthesis of 2'-nitrofolic acid (a) Synthesis of 4-(tert-butoxycarbonylamino)-2-nitrobenzoic acid To a suspension of 1 g of 4-amino-2-nitro-benzoic acid in 10 ml of water 0.69 g of aqueous sodium hydroxide solution (32%) were added followed by a solution of 1.2 g di-tert.-butyl-dicarbonate in 12 ml of dioxane. After 29 hours at room temperature additional 0.24 g of di-tert.-butyl-dicarbonate were added and the mixture was stirred for further 2 hours at room temperature. The reaction mixture was washed three times with methyl-tert.butylether. The aqueous layer was treated with a 10% aqueous solution of citric acid until pH=3 was obtained. The resulting suspension was cooled to 0° C. The product was sucked off, washed with water and dried at 40° C. under vacuum to give 0.72 g of 4-(tert-butoxycarbonylamino)-2-nitrobenzoic acid.

(b) Synthesis of di-tert-butyl-N-(4-(tert.-butoxycarbonylamino)-2-nitrobenzamido)-L-glutamate To a mixture of 4-(tert-butoxycarbonylamino)-2-nitrobenzoic acid in 60 ml of dichloromethane were added 4.8 g of N,N,N',N'-tetramethyl-O-(1H-benzotriazol-1-yl)-uronium-hexafluoro-phosphate. After stirring for 15 min. a mixture of 3.8 g of L-glutamic acid-di tert.-butylester hydrochloride in 60 ml dichloromethane and 3 ml triethylamin was added dropwise. After stirring for 20 hours at room temperature, the mixture was filtered and the filtrate was washed five times with 10% aqueous citric acid, four times with 5% aqueous sodium carbonate solution and two times with water. The organic layer was dried over magnesium sulphate and concentrated in vacuum to give 6.3 g of di-tert-butyl N-(4-(tert-butoxycarbonylamino)-2-nitrobenzamido)-L-glutamate as a yellow foam. This was directly used in example 3.

(c) N-(4-amino-2-nitrobenzamido)-L-glutamic acid×trifluoroacetic acid salt

To a solution of di-tert.-butyl-N-(4-(tert-butoxycarbonylamino)-2-nitrobenzamido)-L-glutamate in 53 ml dichloromethane were added 53 ml of trifluoroacetic acid at 0° C. under argon. After 1 hour at room temperature the mixture was concentrated to dryness to give 3.54 g of N-(4-amino-2-nitrobenzamido)-L-glutamic acid as a yellow foam.

(d) Synthesis of 2'-nitrofolic acid

To a solution of 3.5 g of N-(4-amino-2-nitrobenzamido)-L-glutamic acid×trifluoroacetic acid salt in 50 ml of dimethylacetamide 2.31 g of 2-amino-4-oxo-6-brommethyl-pteridine hydrobromide were added under nitrogen atmosphere. The suspension was stirred at 60° C. for 5 hours and then for 20 hours at room temperature. Solids were removed by filtration and washed with dimethylacetamide. The filtrate was added dropwise within 10 min. to 321 ml of 0.1 M aqueous hydrochloric acid at room temperature. The resulting suspension was stirred for 2 hours at room temperature. The product was sucked off, washed with 24 ml of 0.1 M aqueous hydrochloric acid, 24 ml of water, dried at 40° C. under vacuum to give 1.54 g of crude 2'-nitrofolic acid which was purified by recrystallization from water to give 1.04 g of pure 2'-nitrofolic acid. (HPLC purity: 98.1% area, m/z=487 [M+1]$^+$, $^1$H-NMR (200 MHz, DMSO-d$_6$) [ppm]: 8.65 (s, C(7)-H, 1H); 7.75 (t, N(8')-H, 1H, exchangeable with D$_2$O); 7.51 (t, C(3'H), 1H); 7.20 (t, N(10)-H, 1H, exchangeable with D$_2$O); 7.03 (bs, NH$_2$, 2H, exchangeable with D$_2$O); 6.50 (m, C(5')-H, (C(6')-H, 2H); 4.48 (d, C(6)H$_2$, 2H); 4.29 (m, C(α)-H, 1H); 2.28 (m, C(β)-H$_2$, 2H); 1.96 (m, C(γ)-H$_2$, 2H).

Example 2: Synthesis of 2'-nitrofolic acid dimethyl ester benzenesulfonate

Esterification of 2'nitrofolic acid was achieved in analogy to the method described for esterification of folic acid in WO 2001/04121.

Example 3: Synthesis of N$^2$,N,N-dimethylaminomethylene-2'-nitrofolic acid-di-tert. butylester (a) Synthesis of 4-(((9H-fluorene-9-yl)methoxy) carbonylamino)-2-nitrobenzoic acid To a solution of 11.4 g 4-amino-2-nitro-benzoic acid in 228 ml of water containing 6.63 g of sodium carbonate were added 17.0 g of 9-fluorenylmethyl-chloroformate and dropwise 20 ml of dioxane. After stirring for 20 hours under nitrogen, the mixture was filtered and the filtrate was washed five times with methyl-tert.-butylether. Residual methyl-tert.-butylether was removed from the aqueous phase by evaporation under vacuum. To the aqueous phase were added 456 g of 0° C. cold water. The mixture was adjusted to pH=3 by addition of 31 ml of 2M aqueous hydrochloric acid. The precipitate was sucked off, washed with 513 ml of water, dried at 40° C. in vacuum to give 17.0 g of 4-(((9H-fluorene-9-yl)methoxy)carbonylamino)-2-nitrobenzoic acid as off-white crystals.

(b) Synthesis of di-tert-butyl-N-(4-(((9H-fluorene-9-yl)methoxy)carbonylamino)-2-nitrobenzamido)-L-glutamate To a suspension of 17.2 g 4-(((9H-fluorene-9-yl)methoxy) carbonylamino)-2-nitrobenzoic acid in 222 ml dichloromethane were added 17.7 g of N,N,N',N'-tetramethyl-O-(1H-benzotriazol-1-yl)-uronium-hexafluoro-phosphate. After stirring for 15 min. at room temperature a solution of 13.8 g of L-glutamic acid-di-tert.butylester hydrochloride in 172 ml dichloromethane and 12.9 ml triethylamine were added dropwise within 30 min. The mixture was stirred under nitrogen at room temperature for 20 hours. After addition of 860 ml of methyl-tert.-butylether the mixture was washed five times with aqueous sodium H carbonate (5%), 5 times with aqueous citric acid (5%) and two times with brine. The organic layer was dried over magnesium sulphate and evaporated to dryness under vacuum to give 27.9 g of crude di-tert-butyl 2-(4-(((9H-fluorene-9-yl) methoxy)carbonylamino)-2-nitrobenzamido)-L-glutamate as a yellow foam. The crude product was purified by flash chromatography using silica gel 60 and ethylacetate/n-heptane/45:55 as eluent. After evaporation of product fractions 23.8 g of di-tert-butyl-N-(4-(((9H-fluorene-9-yl)methoxy) carbonylamino)-2-nitrobenzamido)-L-glutamate were obtained as a yellow foam (HPLC, purity: 99.9% area).

(c) Synthesis of N-(4-amino-2-nitrobenzamido)-L-glutamic acid di-tert.-butylester To a mixture of 10 g of di-tert-butyl N-(4-(((9H-fluorene-9-yl)methoxy)carbonylamino)-2-nitrobenzamido)-L-glutamate in 200 ml of N,N-dimethylformamide 1.34 ml pyrrolidine were added. The mixture was stirred for 30 min. at room temperature and then evaporated to dryness under vacuum. After addition of 200 ml of diisopropylether and stirring for 15 min., the resulting suspension was kept at 0° C. over night. The product was sucked-off, washed with 60 ml of diisopropylether and then dried under vacuum to give 4.3 g of N-(4-amino-2-nitrobenzamido)-L-glutamic acid di-tert.-butylester as yellow needles (HPLC, assay 99.7% area).

(d) Synthesis of 2'-nitrofolic acid-di-tert.-butylester

To a solution of 1 g of N-(4-amino-2-nitrobenzamido)-L-glutamic acid di-tert.-butylester in 100 ml of dimethylacetamide were added 2.1 g of 2-amino-4-oxo-6-brommethyl-pteridine hydrobromide. The mixture was stirred under nitrogen at 60° C. for 13 hours. After cooling to room temperature, the mixture was filtered and the filtrate was added dropwise to 700 ml of water. The crystals were sucked off, washed with 70 ml of water and dried at 35° C. under vacuum to give 1.12 g of 2'-nitrofolic acid-di-tert.-butylester.

(e) Synthesis of $N^2$,N,N-dimethylaminomethylene-2'-nitrofolic acid-di-tert.-butylester To a solution of 1 g of 2'-nitrofolic acid-di-tert.-butylester in 150 ml dry dimethylformamide were added 3.5 ml of diisopropyldimethylacetal. The mixture was stirred under nitrogen for 20 hours at room temperature and was then evaporated to dryness. The residue was purified by flash chromatography using silica gel 60 and dichloromethane/methanol/95:5 as eluent to give 0.62 g of $N^2$,N,N-dimethylaminomethylene-2'-nitrofolic acid-di-tert.-butylester.

Example 4: Synthesis of $N^2$,N,N-dimethylaminomethylene-2'-nitrofolic acid-dimethyl ester

(a) Synthesis of dimethyl-N-(4-(tert.-butoxycarbonylamino)-2-nitrobenzamido)-L-glutamate The synthesis was achieved in analogy to example 2 by using L-glutamic acid-dimethylester-hydrochloride instead of the L-glutamic acid-di-tert.-butylester-hydrochloride. From 14.8 g of 4-(tert-butoxycarbonylamino)-2-nitrobenzoic acid 27.4 g of crude dimethyl-N-(4-(tert.-butoxycarbonylamino)-2-nitrobenzamido)-L-glutamate were obtained which were purified twice by flash chromatography using silicagel 60 and ethylacetate/n-heptane/65:35 as eluent. After purification 17.38 g of dimethyl-N-(4-(tert.butoxycarbonylamino)-2-nitrobenzamido)-L-glutamate were obtained.

(b) Synthesis of N-(4-amino-2-nitrobenzamido)-L-glutamic acid-dimethylester×trifluoroacetic acid salt The synthesis was achieved in analogy to example 3. From 17 g of dimethyl-N-(4-(tert.-butoxycarbonylamino)-2-nitrobenzamido)-L-glutamate 19.5 g of N-(4-amino-2-nitrobenzamido)-L-glutamic acid-dimethylester×trifluoroacetic acid salt were obtained which were used directly in example 4(c).

(c) Synthesis of 2'-nitrofolic acid dimethylester

The synthesis was performed in analogy to example 8 starting from 5 g of N-(4-amino-2-nitrobenzamido)-L-glutamic acid-dimethylester×trifluoroacetic acid salt. The work-up was modified as follows. After filtration of the reaction mixture the filtrate was added dropwise to 3.5 l of 0.1 M aqueous hydrochloric acid. The mixture was kept at 0° C. over night and the product was sucked-off, washed with 50 ml of 0.1 M aqueous hydrochloric acid, 300 ml of water and then dried at 40° C. in vacuum to give 2.14 g of crude 2'-nitrofolic acid dimethylester. From the mother liquor further 0.82 g of crude 2'-nitrofolic acid dimethylester were obtained. 2.9 g of crude 2'-nitrofolic acid dimethylester were recrystallized from DMAC to give 2.28 g of pure 2'-nitro folic acid dimethylester.

(d) Synthesis of $N^2$,N,N-dimethylaminomethylene-2'-nitrofolic acid-dimethyl ester This was done in analogy to example 3(e).

Example 5: Synthesis of 2'-fluorofolic acid

The synthesis was done in analogy to the synthesis of 2'-nitrofolic acid following examples 1 to 4. In example 1 4-amino-2-fluoro-benzoic acid was used instead of 4-amino-2-nitrobenzoic acid. (HPLC purity: 97.5% area, m/z=460 [M+1]$^+$, $^1$H-NMR (200 MHz, DMSO-$d_6$) [ppm]: 8.65 (s, C(7)-H, 1H); 7.75 (t, N(8')-H, 1H, exchangeable with D$_2$O); 7.51 (t, C(3'H), 1H); 7.20 (t, N(10)H, 1H, exchangeable with D$_2$O); 7.03 (bs, NH$_2$, 2H, exchangeable with D$_2$O); 6.50 (m, C(5')-H, (C(6')-H, 2H); 4.48 (d, C(6)H$_2$, 2H); 4.31 (m, C($\alpha$)-H, 1H); 2.28 (m, C($\beta$)-H$_2$, 2H); 1.96 (m, C($\gamma$)-H$_2$, 2H).

Example 6: 2'-[$^{18}$F]fluoro-folic acid using 2'-nitrofolic acid

The [$^{18}$F]fluoride which was trapped on an anion exchange cartridge, was directly eluted into a 10 ml sealed reaction vessel using a solution of potassium carbonate (1 mg) and Kryptofix© 2.2.2 (5 mg) in 1.5 ml acetonitrile/water (4:1). At 85-90° C. the solvents were removed by vacuum and a stream of nitrogen. Subsequently, 1 ml of dry acetonitrile was added three times and evaporated to dryness.

To the dry [$^{18}$F]fluoride-cryptate complex the precursor N$^2$,N,N-dimethylaminomethylene-2'-nitrofolic acid di-tert.-butylester (5.2 mg) in 0.2 ml DMF were added. The mixture is heated to 140-145° C. for 20 min.

After cooling, 8 ml water were added and the mixture was passed though a reversed phase cartridge (Sep-Pak® 'C18 plus, Waters AG). The cartridge was washed three times with 8 ml of water and dried 2 min by a stream of nitrogen. The $^{18}$F-labelled protected compound was eluted with 2.5 ml of acetonitrile into another 10 ml sealed reaction vessel. The volume of acetonitrile was reduced to 0.3 ml under reduced pressure, nitrogen stream and slight warming of 80-90° C.

For hydrolysis, 0.5 ml of 4M HCl solution was added and the mixture was heated to 60° C. for 5-10 min. After cooling, the mixture is neutralized by 0.5 ml 4M NaOH solution. 0.5 ml of 0.15M phosphate buffer solution was added and the mixture was filled up with HPLC solvent A to a volume of 5 ml.

Semi-preparative HPLC purification was carried out on a RP18 column (Phenomenex© Gemini 5µ C18, 250×10 mm) using a gradient as follows. Solvent A=0.05M phosphate buffer solution, B=methanol, 0-30 min: A: 99%→40%, 30-40 min: A: 40%→10%, 40-45 min: A: 40%→99%.

The HPLC solvent of the product fraction was evaporated under reduced pressure and a stream of nitrogen at 100° C. For formulation water and 0.15M phosphate buffer solution were added to the dry product and the mixture was sterile filtrated.

Example 7: In vivo and ex vivo studies using 2'-[$^{18}$F]fluoro-folic acid

2'-[$^{18}$F]fluoro-folic acid was applied in ex vivo biodistribution studies using eight nude mice bearing KB xenografts tumors. ~2 MBq of the radiotracer were injected into each animal. In a blockade group 200 µg natural folic acid was injected 10 min prior to the radiotracer. The animals were scarified 90 min post injection. The folate receptor-positive KB tumors show a high specific uptake of the radiotracer with a ratio of 86.6% specific blockade. Furthermore a high specific uptake of 95.5% specific blockade was also found in the kidneys, which are known to express the folate receptor.

FIG. 1 shows the high specific uptake of the 2'-[$^{18}$F] fluorofolic acid in folate receptor-positive tissues.

In vivo PET imaging using the 2'-[$^{18}$F]fluoro-folic acid was performed in nude mice bearing KB xenografts tumors. Ca. 10 MBq of the radiotracer were injected into each animal. In the blockade group 200 µg natural folic acid was injected 10 min prior to the radiotracer. The PET scans were acquired from 30 min to 90 min post injection.

PET studies using 2'-[$^{18}$F]fluoro-folic acid provided excellent images of the KB tumors. Furthermore, the uptake is highly specific and blocked by natural folic acid. A high specific uptake of the radiotracer was also found in the kidney cortex, while no uptake was found in the kidney medulla. This pattern is consistent with the distribution of the folate receptor and points out the high specificity of 2'-[$^{18}$F]fluoro-folic acid.

Figure 1:
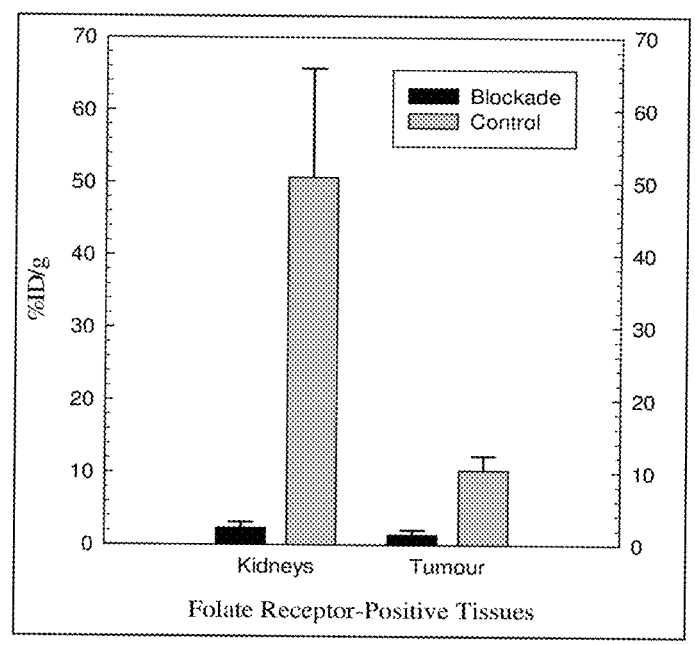
Figure 2:
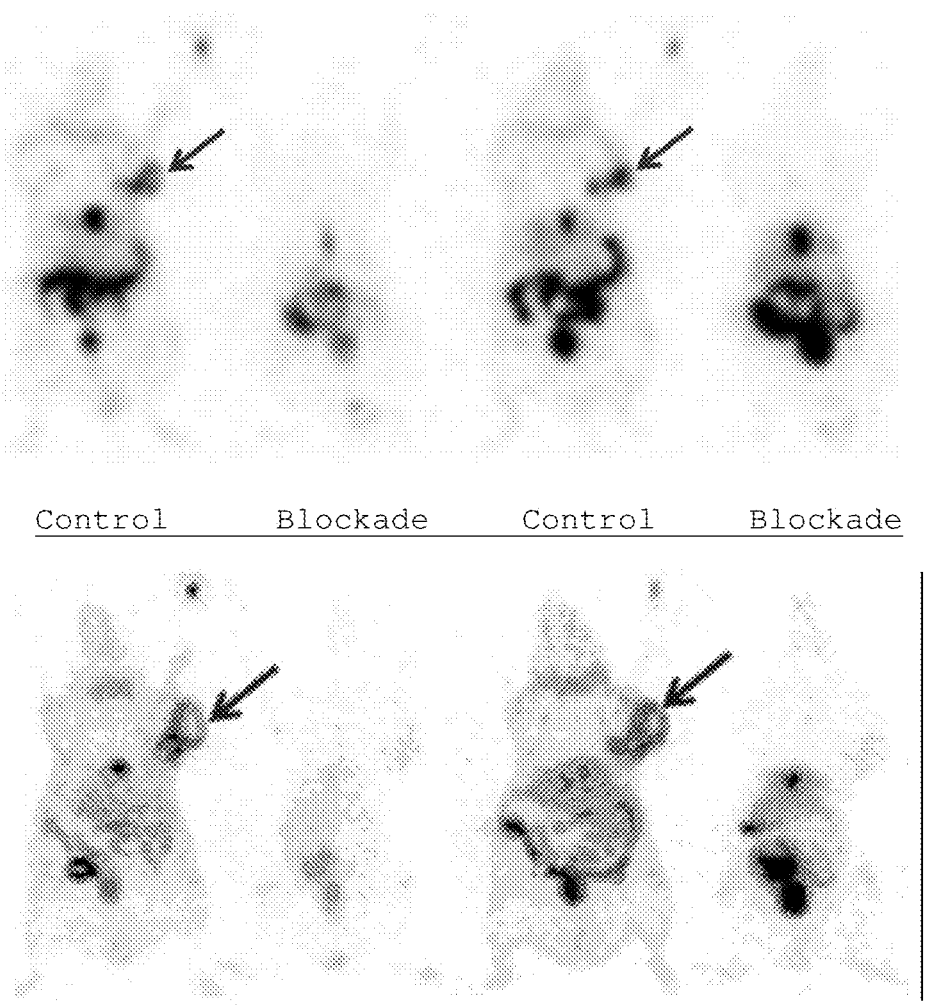
FIG. 2 show PET images using 2'-[$^{18}$F]fluoro-folic acid, the arrows indicate the position of the KB xenografts tumors.
Figure 3:
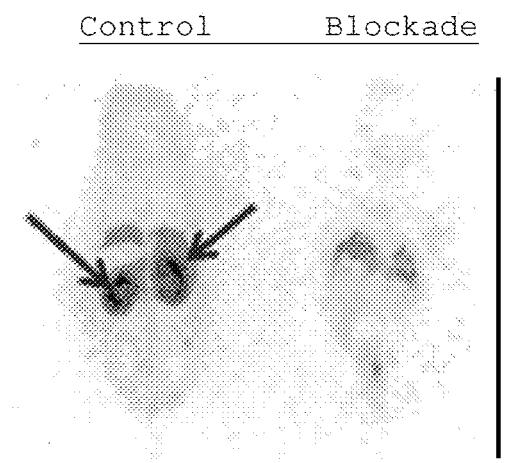
FIG. 3 shows PET images using 2'-[$^{18}$F]fluoro-folic acid, the arrows indicate the kidneys.
Figure 4:
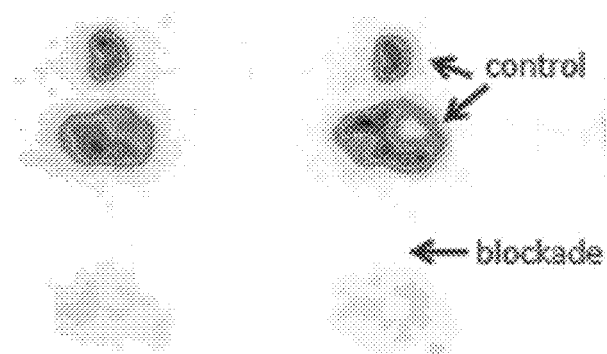
FIG. 4 shows ex vivo PET images of KB xenografts tumors using 2'-[$^{18}$F]fluoro-folic acid.

The invention claimed is:

1. A method for diagnostic imaging of a cell or population of cells expressing a folate-receptor, said method comprising
   (a) administering at least one compound of formula I in an effective amount to achieve diagnostic imaging,

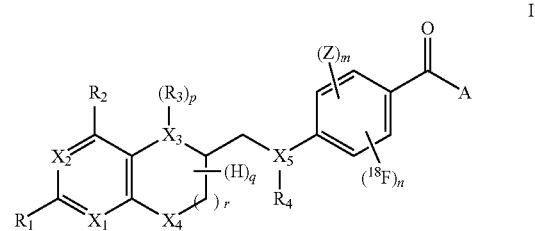

wherein
A is an amino acid,
X$_1$ to X$_5$ are each N,
Z is an electron-withdrawing group,
R$_1$, R$_2$ are independently of each other H, Hal, O, —OR", —NHR", C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl
R" is H or C1-C6 alkyl,
R$_3$, R$_4$ are independently of each other H, formyl, iminomethyl, nitroso, C1-C12 alkyl, C1-C12 alkoxy, C1-C12 alkanoyl, halosubstituted C1-C12 alkanoyl,
m is 0, 1, 2 or 3,
n is 1,
p is 0, 1 or 2,
q has a value of 1 to 7, and
r is 0 or 1,
and
(b) obtaining a diagnostic image of said cell or population of cells.

2. A method according to claim 1, wherein the diagnostic imaging is performed on a cell or population of cells expressing a folate-receptor in vitro.

3. A method for in vitro detection of a cell expressing the folate receptor in a tissue sample comprising
   (a) contacting said tissue sample with a compound according to formula I in an effective amount and for a sufficient time and condition to allow binding to occur,

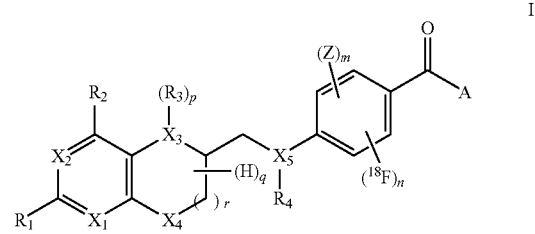

wherein
A is an amino acid,
X$_1$ to X$_5$ are each N,
Z is an electron-withdrawing group, R$_1$, R$_2$ are independently of each other H, Hal, O, —OR", —NHR", C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl R" is H or C1-C6 alkyl, R$_3$, R$_4$ are independently of each other H, formyl, iminomethyl, nitroso, C1-C12 alkyl, C1-C12 alkoxy, C1-C12 alkanoyl, halosubstituted C1-C12 alkanoyl, m is 0, 1, 2 or 3, n is 1, p is 0, 1 or 2, q has a value of 1 to 7, and r is 0 or 1, and (b) detecting such binding.

4. A method of diagnostic imaging or monitoring a subject comprising (a) administering at least one compound according to formula I in an effective amount to achieve diagnostic imaging,

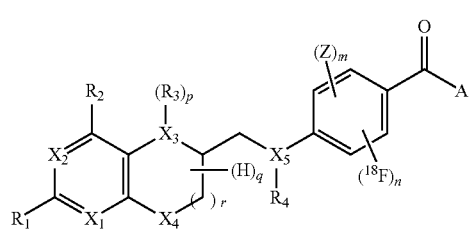

I wherein

A is an amino acid,

X$_1$ to X$_5$ are each N,

Z is an electron-withdrawing group,

R$_1$, R$_2$ are independently of each other H, Hal, O, —OR", —NHR", C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl R" is H or C1-C6 alkyl, R$_3$, R$_4$ are independently of each other H, formyl, iminomethyl, nitroso, C1-C12 alkyl, C1-C12 alkoxy, C1-C12 alkanoyl, halosubstituted C1-C12 alkanoyl, m is 0, 1, 2 or 3, n is 1, p is 0, 1 or 2, q has a value of 1 to 7, and r is 0 or 1, and (b) performing diagnostic imaging using PET by detecting a signal from said at least one compound.

5. A method according to claim 4, which is for monitoring cancer or inflammatory and autoimmune disease therapy in a subject comprising (a) administering to a subject in need thereof at least one compound according to formula I in an effective amount to achieve diagnostic imaging in combination with a therapeutically active compound,

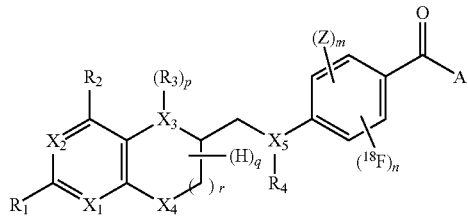

I wherein

A is an amino acid,

X$_1$ to X$_5$ are each N,

Z is an electron-withdrawing group,

R$_1$, R$_2$ are independently of each other H, Hal, O, —OR", —NHR", C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl R" is H or C1-C6 alkyl, R$_3$, R$_4$ are independently of each other H, formyl, iminomethyl, nitroso, C1-C12 alkyl, C1-C12 alkoxy, C1-C12 alkanoyl, halosubstituted C1-C12 alkanoyl, m is 0, 1, 2 or 3, n is 1, p is 0, 1 or 2, q has a value of 1 to 7, and r is 0 or 1, and (b) performing diagnostic imaging using PET by detecting a signal from said at least one compound to follow the course of cancer or inflammatory and autoimmune disease therapy.

6. A method of claim 4 further comprising diagnosis or therapy of cancer or inflammatory and autoimmune disease by a compound other than the compound of formula I.

7. A method according to claim 1, wherein the diagnostic imaging is performed on a cell or population of cells expressing a folate-receptor in vivo.

8. A method according to claim 1, wherein the aminobenzoyl moiety of the compound of formula I is substituted with fluorine-18 in the 2'-position or the 6'-position.

9. A method according to claim 1, wherein the aminobenzoyl moiety of the compound of formula I is substituted with at least one electron-withdrawing group Z in the 2'-position or the 6'-position.

10. A method according to claim 9, wherein the electron-withdrawing group Z is selected from the group consisting of —NO$_2$, —CN, —N$^+$(CH$_3$)$_3$, —SO$_3$R', —COOR', —COR', —Cl, —Br, —F, iodonium salts —I$^+$(R')$_2$, dialkyl/-aryl silanes —SiOH(R')$_2$, and silanols —SiH(R')$_2$, wherein R' is independently a straight-chain or branched C$_{(1-12)}$ alkyl group or an optionally substituted carbocyclic and heterocyclic group comprising five-, six- or ten-membered ring systems.

11. A method according to claim 1, wherein A is an amino acid selected from glutamic acid, aspartic acid, glutamine, aspartine, lysine, arginine, cysteine, and homopolymers thereof.

12. A method according to claim 1, wherein the compound of formula I has formula II,

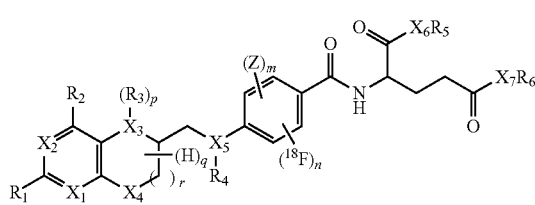

II wherein $X_1$ to $X_5$ are each N, $X_6$, $X_7$ are independently of each other C, N or O, Z is an electron-withdrawing group selected from —$NO_2$, —CN, —$N^+(CH_3)_3$, —$SO_3R'$, —COOR', —COR', —Cl, —Br, —F, iodonium salts —$I^+(R')_2$, dialkyl/-aryl silanes —$SiOH(R')_2$, and silanols —$SiH(R')_2$, R' is independently a straight-chain or branched $C_{(1-12)}$ alkyl group or an optionally substituted carbocyclic and heterocyclic group comprising five-, six- or ten-membered ring systems, $R_1$, $R_2$ are independently of each other H, Hal, O, —OR", —NHR", C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, R" is H or C1-C6 alkyl, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, $R_5$, $R_6$ are independently of each other H or straight chain or branched $C_1$-$C_{12}$ alkyl, which is unsubstituted or substituted by at least one CN, Hal, or $NO_2$, and wherein one or more of embedded, non-adjacent CH2 groups may independently be replaced by —O—, —CO—, —CO—O—, —CO—NR'—, —CH═CH—, —C≡C—, m is 0, 1, 2 or 3, n is 1, r is 0 or 1, p is 0, 1 or 2, and q has a value of 1 to 7.

13. A method according to claim 12, wherein the fluorine-18 is at the 2'- or 6'-position.

14. A method according to claim 1, wherein the compound of formula I has formulae III or IV,

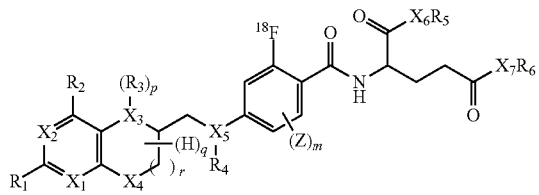

III

-continued

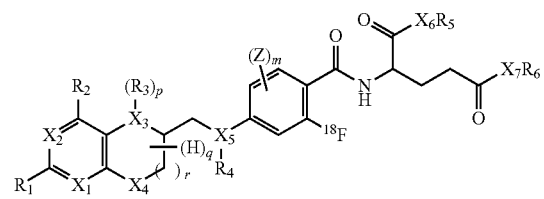

IV wherein $X_1$ to $X_5$ are each N, $X_6$, $X_7$ are independently of each other C, N or O, Z is an electron-withdrawing group selected from —$NO_2$, —CN, —$N^+(CH_3)_3$, —$SO_3R'$, —COOR', —COR', —Cl, —Br, —F, iodonium salts —$I^+(R')_2$, dialkyl/-aryl silanes —$SiOH(R')_2$, and silanols —$SiH(R')_2$, R' is independently a straight-chain or branched $C_{(1-12)}$ alkyl group or an optionally substituted carbocyclic and heterocyclic group comprising five-, six- or ten-membered ring systems, $R_1$, $R_2$ are independently of each other H, Hal, O, —OR", —NHR", C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, R" is H or C1-C6 alkyl, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, $R_5$, $R_6$ are independently of each other H or straight chain or branched $C_1$-$C_{12}$ alkyl, which is unsubstituted or substituted by at least one CN, Hal, or $NO_2$, and wherein one or more of embedded, non-adjacent CH2 groups may independently be replaced by —O—, —CO—, —CO—O—, —CO—NR'—, —CH═CH—, —C≡C—, m is 0, 1, 2, or 3, r is 0 or 1, p is 0, 1 or 2, and q has a value of 1 to 7.

15. A method according to claim 1, wherein the compound of formula I has formulae V or VI,

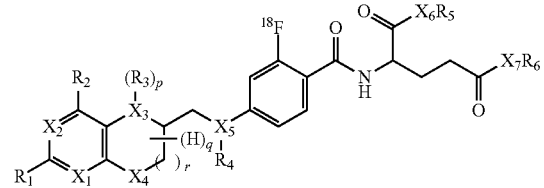

V

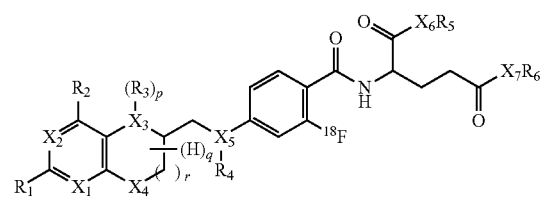

VI wherein $X_1$ to $X_5$ are each N, $X_6$, $X_7$ are independently of each other C, N or O, $R_1$, $R_2$ are independently of each other H, Hal, O, —OR",
—NHR", C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, R" is H or C1-C6 alkyl, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, $R_5$, $R_6$ are independently of each other H or straight chain or branched $C_1$-$C_{12}$ alkyl, which is unsubstituted or substituted by at least one CN, Hal, or $NO_2$, and wherein one or more of embedded, non-adjacent CH2 groups may independently be replaced by —O—, —CO—, —CO—O—, —CO—NR'—, —CH=CH—, —C≡C—, r is 0 or 1, p is 0, 1 or 2, and q has a value of 1 to 7.

16. A method according to claim 1, wherein the compound of formula I has formulae VII, VIII, IX, X or XI,

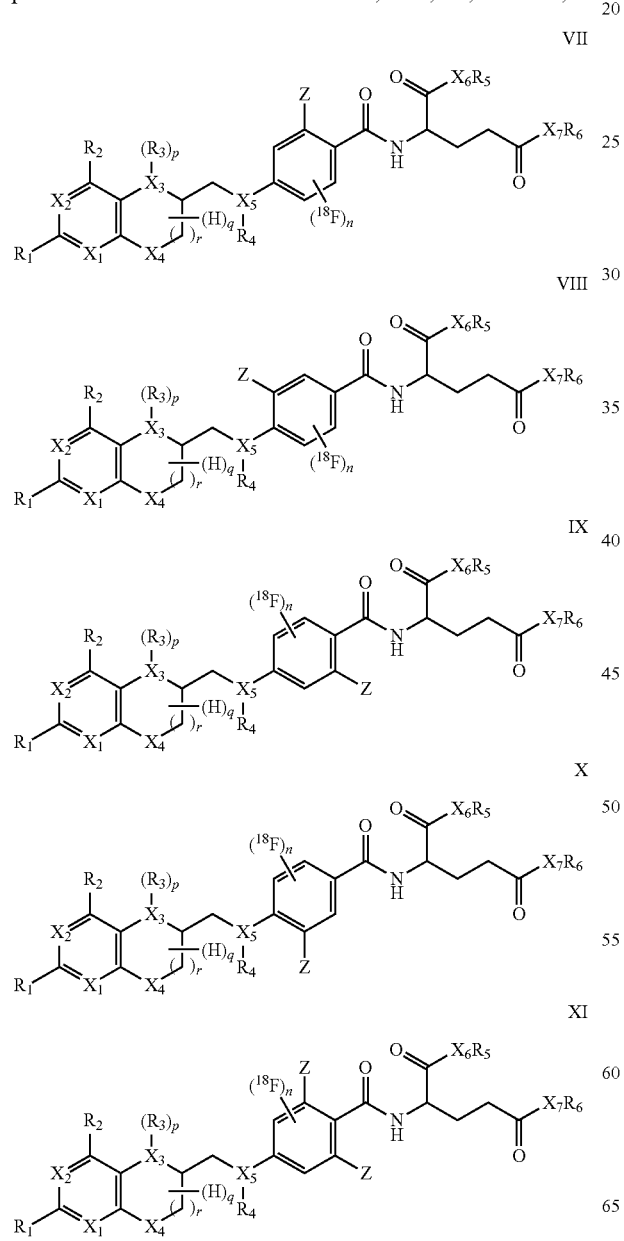

wherein $X_1$ to $X_5$ are each N, $X_6$, $X_7$ are independently of each other C, N or O, Z is an electron-withdrawing group selected from —$NO_2$, —CN, —$N^+(CH_3)_3$, —$SO_3R'$, —COOR', —COR', —Cl, —Br, —F, iodonium salts —$I^+(R')_2$, dialkyl/-aryl silanes —$SiOH(R')_2$, and silanols —$SiH(R')_2$, R' is independently a straight-chain or branched $C_{(1-12)}$ alkyl group or an optionally substituted carbocyclic and heterocyclic group comprising five-, six- or ten-membered ring systems, $R_1$, $R_2$ are independently of each other H, Hal, O, —OR", —NHR", C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, R" is H or C1-C6 alkyl, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, $R_5$, $R_6$ are independently of each other H or straight chain or branched $C_1$-$C_{12}$ alkyl, which is unsubstituted or substituted by at least one CN, Hal, or $NO_2$, and wherein one or more of embedded, non-adjacent CH2 groups may independently be replaced by —O—, —CO—, —CO—O—, —CO—NR'—, —CH=CH—, —C≡C—, n is 1, r is 0 or 1, p is 0, 1 or 2, and q has a value of 1 to 7.

17. A method according to claim 1, wherein the compound of formula I has formula XV,

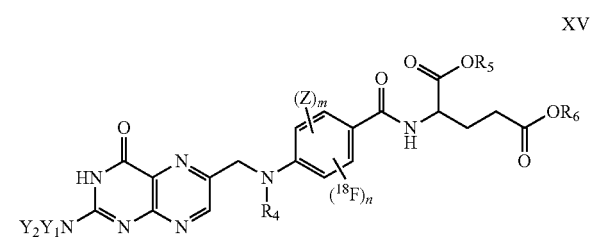

wherein

Z is an electron-withdrawing group selected from —$NO_2$, —CN, —$N^+(CH_3)_3$, —$SO_3R'$, —COOR', —COR', —Cl, —Br, —F, iodonium salts —$I^+(R')_2$, dialkyl/-aryl silanes —$SiOH(R')_2$, and silanols —$SiH(R')_2$, R' is independently a straight-chain or branched $C_{(1-12)}$ alkyl group or an optionally substituted carbocyclic and heterocyclic group comprising five-, six- or ten-membered ring systems, $R_5$, $R_6$ are independently of each other H or straight chain or branched $C_1$-$C_{12}$ alkyl, which is unsubstituted or substituted by at least one CN, Hal, or $NO_2$, and wherein one or more of embedded, non-adjacent CH2 groups may independently be replaced by —O—, —CO—, —CO—O—, —CO—NR'—, —CH=CH—, —C≡C—, $Y_1$, $Y_2$ are independently of each other selected from H or straight chain or branched $C_1$-$C_6$ alkyl, $R_4$ is selected from H, nitroso, $C_1$-$C_{12}$ alkyl, $C_1$-$C_{12}$ alkoxy, $C_1$-$C_{12}$ alkanoyl, halosubstituted $C_1$-$C_{12}$ alkanoyl, m is 0, 1, 2 or 3, and n is 1.

18. A method according to claim 1, wherein the compound of formula I has formula XVI,

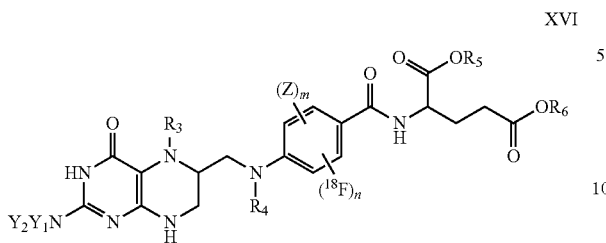

wherein
- Z is an electron-withdrawing group selected from —NO$_2$, —CN, —N$^+$(CH$_3$)$_3$, —SO$_3$R', —COOR', —COR', —Cl, —Br, —F, iodonium salts —I$^+$(R')$_2$, dialkyl/-aryl silanes —SiOH(R')$_2$, and silanols —SiH(R')$_2$,
- R' is independently a straight-chain or branched C$_{(1-12)}$ alkyl group or an optionally substituted carbocyclic and heterocyclic group comprising five-, six- or ten-membered ring systems,
- R$_3$, R$_4$ are independently of each other H, formyl, iminomethyl, nitroso, C1-C12 alkyl, C1-C12 alkoxy, C1-C12 alkanoyl, halosubstituted C1-C12 alkanoyl,
- R$_5$, R$_6$ are independently of each other H or straight chain or branched C$_1$-C$_{12}$ alkyl, which is unsubstituted or substituted by at least one CN, Hal, or NO$_2$, and wherein one or more of embedded, non-adjacent CH2 groups may independently be replaced by —O—, —CO—, —CO—O—, —CO—NR'—, —CH═CH—, —C≡C—,
- Y$_1$, Y$_2$ are independently of each other selected from H or straight chain or branched C$_1$-C$_6$ alkyl,
- m is 0, 1, 2 or 3, and
- n is 1.

19. A method according to claim 1, wherein the compound of formula I has formula XVII,

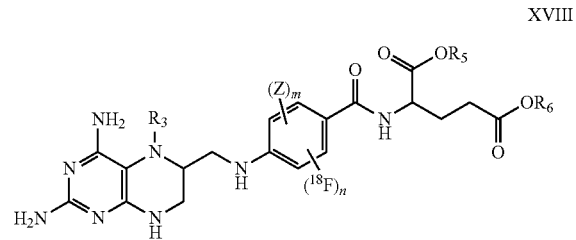

wherein
Z is an electron-withdrawing group selected from —NO$_2$, —CN, —N$^+$(CH$_3$)$_3$, —SO$_3$R', —COOR', —COR', —Cl, —Br, —F, iodonium salts —I$^+$(R')$_2$, dialkyl/-aryl silanes —SiOH(R')$_2$, and silanols —SiH(R')$_2$,
- R' is independently a straight-chain or branched C$_{(1-12)}$ alkyl group or an optionally substituted carbocyclic and heterocyclic group comprising five-, six- or ten-membered ring systems
- R$_5$, R$_6$ are independently of each other H or straight chain or branched C$_1$-C$_{12}$ alkyl, which is unsubstituted or substituted by at least one CN, Hal, or NO$_2$, and wherein one or more of embedded, non-adjacent CH2 groups may independently be replaced by —O—, —CO—, —CO—O—, —CO—NR'—, —CH═CH—,
- m is 0, 1, 2 or 3, and
- n is 1.

20. A method according to claim 1, wherein the compound of formula I has formula

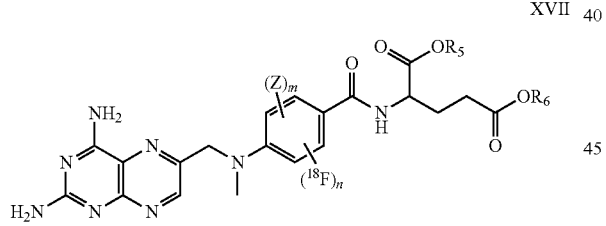

wherein,
- Z is an electron-withdrawing group preferably selected from —NO$_2$, —CN, —N$^+$(CH$_3$)$_3$, —SO$_3$R', —COOR', —COR', —Cl, —Br, —F, iodonium salts —I$^+$(R')$_2$, dialkyl/-aryl silanes —SiOH(R')$_2$, and silanols —SiH(R')$_2$,
- R' is independently a straight-chain or branched C$_{(1-12)}$ alkyl group or an optionally substituted carbocyclic and heterocyclic group comprising five-, six- or ten-membered ring systems,
- R$_3$ is H, methyl- or formyl-,
- R$_5$, R$_6$ are independently of each other H or straight chain or branched C$_1$-C$_{12}$ alkyl, which is unsubstituted or substituted by at least one CN, Hal, or NO$_2$, and wherein one or more of embedded, non-adjacent CH2 groups may independently be replaced by —O—, —CO—, —CO—O—, —CO—NR'—, —CH═CH—, —C≡C—,
- m is 0, 1, 2 or 3, and
- n is 1.

21. A method according to claim 1, wherein the diagnostic imaging is performed on a tissue sample.

* * * * *